(12) United States Patent
Csiszovszki et al.

(10) Patent No.: US 10,973,909 B1
(45) Date of Patent: Apr. 13, 2021

(54) CORONAVIRUS VACCINE

(71) Applicant: PepTC Vaccines Limited, London (GB)

(72) Inventors: Zsolt Csiszovszki, Budapest (HU); Orsolya Lőrincz, Budapest (HU); Levente Molnár, Felsőpakony (HU); Péter Páles, Budapest (HU); Katalin Pántya, Budapest (HU); Eszter Somogyi, Balatonalmádi (HU); József Tóth, Győr (HU); Enikő R. Tőke, Felsőpakony (HU)

(73) Assignee: PepTC Vaccines Limited, London (GB)

( * ) Notice: Subject to any disclaimer, the term of this patent is extended or adjusted under 35 U.S.C. 154(b) by 0 days.

(21) Appl. No.: 16/842,669

(22) Filed: Apr. 7, 2020

(30) Foreign Application Priority Data

Apr. 3, 2020 (GB) ..................................... 2004974

(51) Int. Cl.
  *A61K 39/215* (2006.01)
  *A61K 39/39* (2006.01)
  *C07K 14/73* (2006.01)
  *C07K 14/74* (2006.01)
  *C07K 14/705* (2006.01)

(52) U.S. Cl.
  CPC ............ *A61K 39/215* (2013.01); *A61K 39/39* (2013.01); *C07K 14/70514* (2013.01); *C07K 14/70517* (2013.01); *C07K 14/70539* (2013.01)

(58) Field of Classification Search
  CPC .................. A61K 39/215; A61K 39/39; C07K 14/70517; C07K 14/70514; C07K 14/70539
  See application file for complete search history.

(56) References Cited

U.S. PATENT DOCUMENTS

| | | | |
|---|---|---|---|
| 4,235,877 A | 11/1980 | Fullerton | |
| 7,820,786 B2 | 10/2010 | Thomson et al. | |
| 10,213,497 B2 | 2/2019 | Lisziewicz et al. | |
| 2004/0209324 A1 | 10/2004 | Koren et al. | |
| 2005/0100883 A1* | 5/2005 | Wang ............... | G01N 33/56983 435/5 |
| 2006/0257852 A1* | 11/2006 | Rappuoli ............. | A61K 39/12 435/5 |
| 2010/0074925 A1 | 3/2010 | Carmon et al. | |
| 2016/0199469 A1 | 7/2016 | Georges et al. | |
| 2017/0096455 A1* | 4/2017 | Baric ..................... | A61P 31/12 |
| 2018/0264094 A1 | 9/2018 | Lisziewicz et al. | |
| 2018/0264095 A1* | 9/2018 | Lisziewicz ....... | A61K 39/39558 |
| 2019/0240302 A1 | 8/2019 | Lisziewicz et al. | |
| 2020/0069786 A1 | 3/2020 | Molnar et al. | |

FOREIGN PATENT DOCUMENTS

| | | |
|---|---|---|
| EP | 2042600 A1 | 4/2009 |
| EP | 2745845 A1 | 6/2014 |
| EP | 3369431 A1 | 9/2018 |
| EP | 3370065 A1 | 9/2018 |
| WO | WO-0018238 A1 | 4/2000 |
| WO | WO-0056365 A1 | 9/2000 |
| WO | 0190197 A1 | 11/2001 |
| WO | WO-0190197 A1 | 11/2001 |
| WO | 2015033140 A1 | 3/2015 |
| WO | WO-2015033140 A1 | 3/2015 |
| WO | WO-2015164798 A1 | 10/2015 |
| WO | WO-2016040900 A1 | 3/2016 |
| WO | WO-2016090177 A1 | 6/2016 |
| WO | WO-2016172722 A1 | 10/2016 |
| WO | WO-2018158455 A1 | 9/2018 |
| WO | WO-2018158456 A1 | 9/2018 |
| WO | WO-2018158457 A1 | 9/2018 |

OTHER PUBLICATIONS

Padron-Regalado E. Vaccines for SARS-CoV-2: Lessons from Other Coronavirus Strains. Infect Dis Ther. Apr. 23, 2020;9(2):1-20. Epub ahead of print.*
Gerdts V, Zakhartchouk A. Vaccines for porcine epidemic diarrhea virus and other swine coronaviruses. Vet Microbiol. Jul. 2017;206:45-51. Epub Dec. 2, 2016.*
Ahmed SF, Quadeer AA, McKay MR. Preliminary Identification of Potential Vaccine Targets for the COVID-19 Coronavirus (SARS-CoV-2) Based on SARS-CoV Immunological Studies. Viruses. Feb. 25, 2020;12(3):254. doi: 10.3390/v12030254. PMID: 32106567; PMCID: PMC7150947.*
Wu F, et. al. Severe acute respiratory syndrome coronavirus 2 isolate Wuhan-Hu-1, complete genome. NCBI Reference Sequence: NC_045512.2, Rev. Jan. 28, 2020.*
Somogyi E, Csiszovszki Z, Molnár L, Lőrincz O, et. al.Peptide vaccine candidate mimics the heterogeneity of natural SARS-CoV-2 immunity in convalescent humans and induces broad T cell responses in mice models. Online Oct. 16, 2020. bioRxiv 2020.10.16.339937;doi: https://doi.org/10.1101/2020.10.16.339937.*
Asahara et al. Phase I/II clinical trial using HLA-A24-restricted peptide vaccine derived from KIF20A for patients with advanced pancreatic cancer. J Transl Med 11:291 (2013).
Bagarazzi et al. Immunotherapy against HPV16/18 generates potent TH1 and cytotoxic cellular immune responses. Sci Trans Med 4(155):155ra138 (2012).
Batra et al. Epidermal growth factor ligand-independent, unregulated, cell-transforming potential of a naturally occurring human mutant EG1-RvIII gene. Cell Growth Differ 6:1251-1259 (1995).

(Continued)

Primary Examiner — Rachel B Gill
(74) Attorney, Agent, or Firm — Goodwin Procter LLP

(57) ABSTRACT

The disclosure relates to polypeptides, vaccines and pharmaceutical compositions that find use in the prevention or treatment of Coronaviridae or SARS-CoV-2 infection. The disclosure also relates to methods of treating or preventing Coronaviridae or SARS-CoV-2 infection in an individual. The polypeptides and vaccines comprise T cell and/or B cell epitopes that are immunogenic in a high percentage of individuals in the human population.

12 Claims, 5 Drawing Sheets

Specification includes a Sequence Listing.

(56) References Cited

OTHER PUBLICATIONS

Bigner et al. Characterization of the epidermal growth factor receptor in human glioma cell lines and xenografts. Cancer Res 50:8017-8022 (1990).
Bioley et al. HLA class I-associated immunodominance affects CTL responsiveness to an ESO recombinant protein tumor antigen vaccine. Clin Cancer Res. 15(1):299-306 (2009).
Butts et al. Randomized phase IIB trial of BLP25 liposome vaccine in stage IIIB and IV non-small-cell lung cancer. J Clin Oncol 23(27):6674-6681 (2005).
Carmon et al. Phase I/II study exploring ImMucin, a pan-major histocompatibility complex, anti-MUC1 signal peptide vaccine, in multiple myeloma patients. Br J Hematol. 169(1):44-56 (2014).
Cathcart et al. A multivalent bcr-abl fusion peptide vaccination trial in patients with chronic myeloid leukemia. Blood 103:1037-1042 (2004).
Chapuis et al. Transferred WT1-reactive CD8+ T cells can mediate antileukemic activity and persist in post-transplant patients. Sci Transl Med. 5(174):174ra27 (2013).
Chen et al. Multiple Cancer/Testis Antigens Are Preferentially Expressed in Hormone-Receptor Negative and High-Grade Breast Cancers. PLoS One 6(3):e17876 (2011).
Chiriva-Internati et al. Identification of AKAP-4 as a new cancer/testis antigen for detection and immunotherapy of prostate cancer. Prostate 72(1):12-23 (2012).
Choi et al. The expression of MAGE and SSX, and correlation of COX2, VEGF, and survivin in colorectal cancer. Anticancer Res 32(2):559-564 (2012).
Chowell et al. Patient HLA class I genotype influences cancer response to checkpoint blockade immunotherapy. Science 359(6375):582-587 (2018).
Chu et al. Receptor dimerization is not a factor in the signalling activity of a transforming variant epidermal growth factor receptor (EG1-RvIII). Biochem J 324:855-861 (1997).
Cusi et al. Phase I trial of thymidylate synthase poly epitope peptide (TSPP) vaccine in advanced cancer patients. Cancer Immunol Immunother 64:1159-1173 (2015).
Durie et al. International uniform response criteria for multiple myeloma. Leukemia 20:1467-1473 (2006).
Eisenhauer et al. New response evaluation criteria in solid tumours: revised RECIST guideline (version 1.1). Euro J Cancer 45:228-247 (2009).
Fenoglio et al. A multi-peptide, dual-adjuvant telomerase vaccine (GX301) is highly immunogenic in patients with prostate and renal cancer. Cancer Immunol Immunother 62:1041-1052 (2013).
Goel et al. CDK4/6 inhibition triggers anti-tumour immunity. Nature. 548(7668):471-475 (2017).
Goossens-Beumer et al. Clinical prognostic value of combined analysis of Aldh1, Survivin, and EpCAM expression in colorectal cancer. Br J Cancer 110(12):2935-2944 (2014).
Greenfield et al. A phase I dose-escalation clinical trial of a peptidebased human papillomavirus therapeutic vaccine with Candida skin test reagent as a novel vaccine adjuvant for treating women with biopsy-proven cervical intraepithelial neoplasia 2/3. Oncoimmunol 10:e1031439 (2015).
Gudmundsdotter et al. Amplified antigen-specific immune responses in HIV-1 infected individuals in a double blind DNA immunization and therapy interruption trial. Vaccine 29(33):5558-5566 (2011).
Hartmaier et al. Genomic analysis of 63,220 tumors reveals insights into tumor uniqueness and targeted cancer immunotherapy strategies. Genome Med 9:16 (2017).
Hodi et al. Improved survival with ipilimumab in patients with metastatic melanoma. N Engl J Med 363(8):711-723 (2010).
Humphrey et al. Anti-synthetic peptide antibody reacting at the fusion junction of deletion-mutant epidermal growth factor receptors in human glioblastoma. PNAS 87:4207-4211 (1990).
Kaida et al. Phase 1 trial of Wilms tumor 1 (WT1) peptide vaccine and gemcitabine combination therapy in patients with advanced pancreatic or biliary tract cancer. J Immunother 34(1):92-99 (2011).

Kakimi et al. A phase I study of vaccination with NY-ESO-If peptide mixed with Picibanil OK-432 and Montanide ISA-51 in patients with cancers expressing the NY-E50-1 antigen. Int J Cancer 129(12):2836-2846 (2011).
Kanojia et al. Sperm-Associated Antigen 9, a Novel Biomarker for Early Detection of Breast Cancer. Cancer Epidemiol Biomarkers Prev 18(2):630-639 (2009).
Kantoff et al. Overall survival analysis of a phase II randomized controlled trial of a Poxviral-based PSA-targeted immunotherapy in metastatic castration-resistant prostate cancer. J Clin Oncol 28:1099-1105 (2010).
Karkada et al. Therapeutic vaccines and cancer: focus on DPX-0907. Biologics 8:27-38 (2014).
Keilholz et al. A clinical and immunologic phase 2 trial of Wilms tumor gene product 1 (WT1) peptide vaccination in patients with AML and MDS. Blood 113(26):6541-6548 (2009).
Kenter et al. Vaccination against HPV-16 oncoproteins for vulvar intraepithelial neoplasia. N Engl J Med. 361(19):1838-1847 (2009).
Kissler e t al. Projecting the transmission dynamics of SARS-CoV-2 through the post-pandemic period. Available at http://nrs.harvard.edu/urn-3:HUL.InstRepos:42639308 (31 pgs) (2020).
Kovjazin et al. ImMucin: a novel therapeutic vaccine with promiscuous MHC binding for the treatment of MUC1-expressing tumors. Vaccine. 29(29-30):4676-4686 (2011).
Krug et al. WT1 peptide vaccinations induce CD4 and CD8 T cell immune responses in patients with mesothelioma and non-small cell lung cancer. Cancer Immunol Immunother 59(10):1467-1479 (2010).
Kruger et al. Lessons to be learned from primary renal cell carcinomas. Cancer Immunol, Immunother 54:826-836 (2005).
Lammering et al. Inhibition of the type III epidermal growth factor receptor variant mutant receptor by dominant-negative EGFR-CD533 enhances malignant glioma cell radiosensitivity. Clin Cancer Res 10:6732-6743 (2004).
Lammering et al. Radiation-induced activation of a common variant of EGFR confers enhanced radioresistance. Radiother Oncol 72:267-273 (2004).
Li et al. Expression profile of cancer-testis genes in 121 human colorectal cancer tissue and adjacent normal tissue. Clinical Cancer Res 11(5):1809-1814 (2005).
Li et al. Thrombocytopenia caused by the development of antibodies to thrombopoietin. Blood 98:3241-3248 (2001).
Libermann et al. Amplification, enhanced expression and possible rearrangement of EGF receptor gene in primary human brain tumours of glial origin. Nature 313:144-147 (1985).
Montgomery et al. Expression of oncogenic epidermal growth factor receptor family kinases induces paclitaxel resistance and alters 0-tubulin isotype expression. J Biol Chem 275:17358-17363 (2000).
Nagane et al. A common mutant epidermal growth factor receptor confers enhanced tumorigenicity on human glioblastoma cells by increasing proliferation and reducing apoptosis. Cancer Res 56:5079-5086 (1996).
Nishikawa et al. A mutant epidermal growth factor receptor common in human glioma confers enhanced tumorigenicity. PNAS USA 91:7727-7731 (1994).
Okuno et al. Clinical Trial of a 7-Peptide Cocktail Vaccine with Oral Chemotherapy for Patients with Metastatic Colorectal Cancer. Anticancer Res 34:3045-3052 (2014).
Paoletti et al. Potency of clinical group B streptococcal conjugate vaccines. Vaccine 19:2118-2126 (2001).
Pardi et al. mRNA vaccines—a new era in vaccinology. Nat Rev Drug Discov (19 pgs) (2018).
PCT/EP2018/055230 International Search Report and Written Opinion dated Jun. 8, 2018.
PCT/EP2018/055231 International Search Report and Written Opinion dated Apr. 5, 2018.
PCT/EP2018/055232 International Search Report and Written Opinion dated May 9, 2018.
PCT/EP2019/073481 International Search Report and Written Opinion dated Dec. 20, 2019.
Phuphanich et al. Phase I trial of a multi-epitope-pulsed dendritic cell vaccine for patients with newly diagnosed glioblastoma. Cancer Immunol Immunother 62(1):125-135 (2013).

(56) References Cited

OTHER PUBLICATIONS

Rajasagi et al. Systematic identification of personal tumor-specific neoantigens in chronic lymphocytic leukemia. Blood 124(3):453-462 (2014).

Ramakrishnan et al. Chemotherapy enhances tumor cell susceptibility to CTL-mediated killing during cancer immunotherapy in mice. J Clin Invest 120(4):1111-1124 (2010).

Rapoport et al. Combination Immunotherapy after ASCT for Multiple Myeloma Using MAGE-A3/Poly-ICLC Immunizations Followed by Adoptive Transfer of Vaccine-Primed and Costimulated Autologous T Cells. Clin Cancer Res 20(5):1355-1365 (2014).

Rosa et al. Multiple Approaches for Increasing the Immunogenicity of an Epitope-Based Anti-HIV Vaccine. AIDS Res Hum Retroviruses 31(11):1077-1088 (2015).

Saini et al. A Novel Cancer Testis Antigen, A-Kinase Anchor Protein 4 (AKAP4) Is a Potential Biomarker for Breast Cancer. PLoS One 8(2):e57095 (2013).

Sampson et al. Immunologic Escape After Prolonged Progression-Free Survival With Epidermal Growth Factor Receptor Variant III Peptide Vaccination in Patients With Newly Diagnosed Glioblastoma. J Clin Oncol 28:4722-4729 (1994).

Singh et al. Major histocompatibility complex linked databases and prediction tools for designing vaccines. Hum Immunol 77(3):295-306 (2015).

Slingluff et al. Clinical and immunologic results of a randomized phase II trial of vaccination using four melanoma peptides either administered in granulocyte-macrophage colony-stimulating factor in adjuvant or pulsed on dendritic cells. J Clin Oncol 21(21):4016-4026 (2003).

Slingluff et al. Randomized multicenter trial of the effects of melanoma-associated helper peptides and cyclophosphamide on the immunogenicity of a multipeptide melanoma vaccine. J Clin Oncol. 29(21):2924-2932 (2011).

Snyder et al. Genetic basis for clinical response to CTLA-4 blockade in melanoma. N Engl J Med 371(23):2189-2199 (Dec. 4, 2014).

Tagawa et al. Phase I study of intranodal delivery of a plasmid DNA vaccine for patients with Stage IV melanoma. Cancer 98(1):144-154 (2003).

Takedatsu et al. Determination of Thrombopoietin-Derived Peptides Recognized by Both Cellular and Humoral Immunities in Healthy Donors and Patients with Thrombocytopenia. Stem Cells 23(7):975-982 (2005).

Therasse et al. New guidelines to evaluate the response to treatment in solid tumors: European Organization for Research and Treatment of Cancer, National Cancer Institute of the United States, National Cancer Institute of Canada. J Natl Cancer Inst 92:205-216 (2000).

Trimble et al. Safety, efficacy, and immunogenicity of VGX-3100, a therapeutic synthetic DNA vaccine targeting human papillomavirus 16 and 18 E6 and E7 proteins for cervical intraepithelial neoplasia 2/3: a randomised, double-blind, placebo-controlled phase 2b trial. Lancet 386(10008):2078-2088 (2015).

Tsuchida et al. Response evaluation criteria in solid tumors (RECIST): New guidelines. Med Pediatr Oncol 37:1-3 (2001).

U.S. Appl. No. 15/910,988 Office Action dated May 18, 2018.

Valmori et al. Vaccination with NY-ESO-1 protein and CpG in Montanide induces integrated antibody/Th1 responses and CD8 T cells through cross-priming. PNAS USA 104(21):8947-8952 (2007).

Van Allen et al. Genomic correlates of response to CTLA-4 blockade in metastatic melanoma. Science 350:207-211 (2015).

Wada et al. Vaccination with NY-E50-1 overlapping peptides mixed with Picibanil OK-432 and montanide ISA-51 in patients with cancers expressing the NY-E50-1 antigen. J Immunother 37(2):84-92 (2014).

Walter et al. Multipeptide immune response to cancer vaccine IMA901 after single-dose cyclophosphamide associates with longer patient survival. Nat Med. 18(8):1254-1261 (2012).

Wei et al. Screening of single-chain variable fragments against TSP50 from a phage display antibody library and their expression as soluble proteins. J Biol Med Screen 11(5):546-552 (2006).

Weller at al. Rindopepimut with temozolomide for patients with newly diagnosed, EGFRvIII-expressing glioblastoma (Act IV): a randomised, double-blind, international phase 3 trial. Lancet Oncol 18(10):1373-1385 (2017).

Welters et al. Induction of tumor-specific CD4+ and CD8+ T-cell immunity in cervical cancer patients by a human papillomavirus type 16 E6 and E7 long peptides vaccine. Clin. Cancer Res. 14(1):178-187 (2008).

Welters et al. Success or failure of vaccination for HPV16-positive vulvar lesions correlates with kinetics and phenotype of induced T-cell responses. PNAS 107(26):11895-11899 (2010).

Yamada et al. Phase I clinical study of a personalized peptide vaccination available for six different human leukocyte antigen (HLA-A2,-A3,-A11,-A24,-A31 and-A33)-positive patients with advanced cancer. Experimental and Therapeutic Medicine 2(1):109-117 (2011).

Yoshitake et al. Phase II clinical trial of multiple peptide vaccination for advanced head and neck cancer patients revealed induction of immune responses and improved OS. Clin Cancer Res 21(2):312-321 (2014).

Yuan et al. Integrated NY-ESO-1 antibody and CD8+ T-cell responses correlate with clinical benefit in advanced melanoma patients treated with ipilimumab. PNAS USA 108(40):16723-16728 (2011).

Yuan et al. Safety and immunogenicity of a human and mouse gp100 DNA vaccine in a phase I trial of patients with melanoma. Cancer Immun 9:5 (2009).

Zheng et al. High expression of testes-specific protease 50 is associated with poor prognosis in colorectal carcinoma. PLoS One 6(7):e22203 (2011).

Celis et al. Identification of potential CTL epitopes of tumor-associated antigen MAGE-1 for five common HLA-A alleles. Mol Immunol. 31(18):1423-30 (1994).

Celis et al. Induction of anti-tumor cytotoxic T lymphocytes in normal humans using primary cultures and synthetic peptide epitopes. PNAS USA 91:2105-2109 (1994).

Celis, E, et al., Identification of potential CTL epitopes of tumor-associated antigen MAGE-1 for five common HLA-A alleles, Mol Immunol, 31(18): 1423-1430 (1994).

Celis, E, et al., Induction of anti-tumor cytotoxic T lymphocytes in normal humans using primary cultures and synthetic peptide epitopes, PNAS USA, 91: 2105-2109 (1994).

Chowell, D., et al., Patient HLA class I genotype influences cancer response to checkpoint blockade immunotherapy, Science, 359(6375): 582-587 (2018).

U.S. Appl. No. 16/559,430 Office Action dated Apr. 27, 2020.

U.S. Appl. No. 16/559,430 Office Action dated Aug. 27, 2020.

Wieczorek, M., et al., Major histocompatibility complex (MHC) class I and MHC class II proteins: conformational plasticity in antigen presentation, Front Immunol, 8: 292 (2017).

Zajac, P., et al., MAGE-A antigens and cancer immunotherapy, Front Immunol, 4: 18 (2017).

Beatty, G.L., et al., Immune escape mechanisms as a guide for cancer immunotherapy, Clin Cancer Res, 21(4): 687-692 (2015).

Berger, T.G., et al., Circulation and homing of melanoma-reactive T cells to both cutaneous and visceral metastases after vaccination with monocyte-derived dendritic cells, Int J Cancer, 111: 229-237 (2004).

Buonaguro, L., et al., Translating tumor antigens into cancer vaccines, Clin Vaccine Immunol, 18(1): 23-34 (2011).

Engelhard, V.H., Structure of peptides associated with MHC class I molecules, Curr Opin Immunol, 6(1): 13-23 (1994).

Guo, H., et al., Different length peptides bind to HLA-Aw68 similarity at their ends but bulge out in the middle, Nature, 360: 364-366 (1992).

HLA Nomenclature, (2015) retrieved from http://hla.alleles.org/nomenclature/stats.html on Mar. 17, 2015.

Kalos, M., et al., Adoptive T cell transfer for cancer immunotherapy in the era of synthetic biology, Immunity, 39:49-60 (2013).

Kerkar, S.P., et al., Cellular constituents of immune escape within the tumor microenvironment, Cancer Res, 72(13): 3125-3130 (2012).

Liu, J., et al., Major histocompatibility complex: interaction with peptides, in eLS, John Wiley & Sons, Ltd: Chichester (2011).

(56) References Cited

OTHER PUBLICATIONS

Ochoa-Garay, J., et al., The ability of peptides to induce cytotoxic T cells in vitro does not strongly correlate with theu affinity for the H-2Ld molecule: implications for vaccine design and immunotherapy, Mol Immunol, 34(3): 273-281 (1997).

Reche, P.A., et al., Definition of MHC supertypes through clustering of MHC peptide binding repertoires, in Nicosia, G., et al., Eds. ICARIS 2004, LNCS 3239: 189-196( (2004).

Repana, D., et al., The network of cancer genes (NCG): a comprehensive catalogue of known and candidate cancer genes from cancer sequencing screens, Genome Biol, 20(1): 1-12 (2019).

Spranger, S., Mechanisms of tumor escape in the context of the T-cell-inflamed and the non-T-cell-inflamed tumor microenvironment, Int Immunol, 28(8): 383-391 (2016).

Valmori, D., et al., Epitope clustering in regions undergoing efficient proteasomal processing defines immunodominant CTL regions of a tumor antigen, Clin Immunol, 122: 163-172 (2007).

Vitale, M., et al., Effect of tumor cells and tumor microenvironment on NK-cell function, Eur J Immunol, 44: 1582-1592 (2014).

\* cited by examiner

SEQUENCE LISTING

<160> NUMBER OF SEQ ID NOS: 125

<210> SEQ ID NO 1
<211> LENGTH: 30
<212> TYPE: PRT
<213> ORGANISM: Severe acute respiratory syndrome coronavirus 2

<400> SEQUENCE: 1

Thr Gln Leu Pro Pro Ala Tyr Thr Asn Ser Phe Thr Arg Gly Val Tyr
1 5 10 15

Tyr Pro Asp Lys Val Phe Arg Ser Ser Val Leu His Ser Thr
20 25 30

<210> SEQ ID NO 2
<211> LENGTH: 30
<212> TYPE: PRT
<213> ORGANISM: Severe acute respiratory syndrome coronavirus 2

<400> SEQUENCE: 2

Gly Val Tyr Tyr Pro Asp Lys Val Phe Arg Ser Ser Val Leu His Ser
1 5 10 15

Thr Gln Asp Leu Phe Leu Pro Phe Phe Ser Asn Val Thr Trp
20 25 30

<210> SEQ ID NO 3
<211> LENGTH: 30
<212> TYPE: PRT
<213> ORGANISM: Severe acute respiratory syndrome coronavirus 2

<400> SEQUENCE: 3

```
Thr Lys Arg Phe Asp Asn Pro Val Leu Pro Phe Asn Asp Gly Val Tyr
1               5                   10                  15

Phe Ala Ser Thr Glu Lys Ser Asn Ile Ile Arg Gly Trp Ile
            20                  25                  30

<210> SEQ ID NO 4
<211> LENGTH: 30
<212> TYPE: PRT
<213> ORGANISM: Severe acute respiratory syndrome coronavirus 2

<400> SEQUENCE: 4

Ser Asn Ile Ile Arg Gly Trp Ile Phe Gly Thr Thr Leu Asp Ser Lys
1               5                   10                  15

Thr Gln Ser Leu Leu Ile Val Asn Asn Ala Thr Asn Val Val
            20                  25                  30

<210> SEQ ID NO 5
<211> LENGTH: 30
<212> TYPE: PRT
<213> ORGANISM: Severe acute respiratory syndrome coronavirus 2

<400> SEQUENCE: 5

Asp Ser Ser Ser Gly Trp Thr Ala Gly Ala Ala Ala Tyr Tyr Val Gly
1               5                   10                  15

Tyr Leu Gln Pro Arg Thr Phe Leu Leu Lys Tyr Asn Glu Asn
            20                  25                  30

<210> SEQ ID NO 6
<211> LENGTH: 30
<212> TYPE: PRT
<213> ORGANISM: Severe acute respiratory syndrome coronavirus 2

<400> SEQUENCE: 6

Cys Phe Thr Asn Val Tyr Ala Asp Ser Phe Val Ile Arg Gly Asp Glu
1               5                   10                  15

Val Arg Gln Ile Ala Pro Gly Gln Thr Gly Lys Ile Ala Asp
            20                  25                  30

<210> SEQ ID NO 7
<211> LENGTH: 30
<212> TYPE: PRT
<213> ORGANISM: Severe acute respiratory syndrome coronavirus 2

<400> SEQUENCE: 7

Arg Ala Arg Ser Val Ala Ser Gln Ser Ile Ile Ala Tyr Thr Met Ser
1               5                   10                  15

Leu Gly Ala Glu Asn Ser Val Ala Tyr Ser Asn Asn Ser Ile
            20                  25                  30

<210> SEQ ID NO 8
<211> LENGTH: 30
<212> TYPE: PRT
<213> ORGANISM: Severe acute respiratory syndrome coronavirus 2

<400> SEQUENCE: 8

Ala Glu Asn Ser Val Ala Tyr Ser Asn Asn Ser Ile Ala Ile Pro Thr
1               5                   10                  15

Asn Phe Thr Ile Ser Val Thr Thr Glu Ile Leu Pro Val Ser
            20                  25                  30

<210> SEQ ID NO 9
<211> LENGTH: 30
```

```
<212> TYPE: PRT
<213> ORGANISM: Severe acute respiratory syndrome coronavirus 2

<400> SEQUENCE: 9

Ala Leu Gln Ile Pro Phe Ala Met Gln Met Ala Tyr Arg Phe Asn Gly
1               5                   10                  15

Ile Gly Val Thr Gln Asn Val Leu Tyr Glu Asn Gln Lys Leu
            20                  25                  30

<210> SEQ ID NO 10
<211> LENGTH: 30
<212> TYPE: PRT
<213> ORGANISM: Severe acute respiratory syndrome coronavirus 2

<400> SEQUENCE: 10

Phe Ala Met Gln Met Ala Tyr Arg Phe Asn Gly Ile Gly Val Thr Gln
1               5                   10                  15

Asn Val Leu Tyr Glu Asn Gln Lys Leu Ile Ala Asn Gln Phe
            20                  25                  30

<210> SEQ ID NO 11
<211> LENGTH: 30
<212> TYPE: PRT
<213> ORGANISM: Severe acute respiratory syndrome coronavirus 2

<400> SEQUENCE: 11

Arg Glu Gly Val Phe Val Ser Asn Gly Thr His Trp Phe Val Thr Gln
1               5                   10                  15

Arg Asn Phe Tyr Glu Pro Gln Ile Ile Thr Thr Asp Asn Thr
            20                  25                  30

<210> SEQ ID NO 12
<211> LENGTH: 30
<212> TYPE: PRT
<213> ORGANISM: Severe acute respiratory syndrome coronavirus 2

<400> SEQUENCE: 12

Arg Ser Lys Gln Arg Arg Pro Gln Gly Leu Pro Asn Asn Thr Ala Ser
1               5                   10                  15

Trp Phe Thr Ala Leu Thr Gln His Gly Lys Glu Asp Leu Lys
            20                  25                  30

<210> SEQ ID NO 13
<211> LENGTH: 30
<212> TYPE: PRT
<213> ORGANISM: Severe acute respiratory syndrome coronavirus 2

<400> SEQUENCE: 13

Ser Lys Lys Pro Arg Gln Lys Arg Thr Ala Thr Lys Ala Tyr Asn Val
1               5                   10                  15

Thr Gln Ala Phe Gly Arg Arg Gly Pro Glu Gln Thr Gln Gly
            20                  25                  30

<210> SEQ ID NO 14
<211> LENGTH: 30
<212> TYPE: PRT
<213> ORGANISM: Severe acute respiratory syndrome coronavirus 2

<400> SEQUENCE: 14

Glu Leu Ile Arg Gln Gly Thr Asp Tyr Lys His Trp Pro Gln Ile Ala
1               5                   10                  15

Gln Phe Ala Pro Ser Ala Ser Ala Phe Phe Gly Met Ser Arg
```

```
                20                  25                  30
```

<210> SEQ ID NO 15
<211> LENGTH: 30
<212> TYPE: PRT
<213> ORGANISM: Severe acute respiratory syndrome coronavirus 2

<400> SEQUENCE: 15

```
Gln Arg Gln Lys Lys Gln Gln Thr Val Thr Leu Leu Pro Ala Ala Asp
1               5                   10                  15

Leu Asp Asp Phe Ser Lys Gln Leu Gln Gln Ser Met Ser Ser
                20                  25                  30
```

<210> SEQ ID NO 16
<211> LENGTH: 30
<212> TYPE: PRT
<213> ORGANISM: Severe acute respiratory syndrome coronavirus 2

<400> SEQUENCE: 16

```
Leu Ser Tyr Phe Ile Ala Ser Phe Arg Leu Phe Ala Arg Thr Arg Ser
1               5                   10                  15

Met Trp Ser Phe Asn Pro Glu Thr Asn Ile Leu Leu Asn Val
                20                  25                  30
```

<210> SEQ ID NO 17
<211> LENGTH: 30
<212> TYPE: PRT
<213> ORGANISM: Severe acute respiratory syndrome coronavirus 2

<400> SEQUENCE: 17

```
Asn Ile Val Asn Val Ser Leu Val Lys Pro Ser Phe Tyr Val Tyr Ser
1               5                   10                  15

Arg Val Lys Asn Leu Asn Ser Ser Arg Val Pro Asp Leu Leu
                20                  25                  30
```

<210> SEQ ID NO 18
<211> LENGTH: 8
<212> TYPE: PRT
<213> ORGANISM: Severe acute respiratory syndrome coronavirus 2

<400> SEQUENCE: 18

```
Ala Met Gln Met Ala Tyr Arg Phe
1               5
```

<210> SEQ ID NO 19
<211> LENGTH: 8
<212> TYPE: PRT
<213> ORGANISM: Severe acute respiratory syndrome coronavirus 2

<400> SEQUENCE: 19

```
Ala Met Gln Met Ala Tyr Arg Phe
1               5
```

<210> SEQ ID NO 20
<211> LENGTH: 15
<212> TYPE: PRT
<213> ORGANISM: Severe acute respiratory syndrome coronavirus 2

<400> SEQUENCE: 20

```
Arg Arg Pro Gln Gly Leu Pro Asn Asn Thr Ala Ser Trp Phe Thr
1               5                   10                  15
```

<210> SEQ ID NO 21

```
<211> LENGTH: 18
<212> TYPE: PRT
<213> ORGANISM: Severe acute respiratory syndrome coronavirus 2

<400> SEQUENCE: 21

Gly Leu Pro Asn Asn Thr Ala Ser Trp Phe Thr Ala Leu Thr Gln His
1               5                   10                  15

Gly Lys

<210> SEQ ID NO 22
<211> LENGTH: 15
<212> TYPE: PRT
<213> ORGANISM: Severe acute respiratory syndrome coronavirus 2

<400> SEQUENCE: 22

Arg Arg Pro Gln Gly Leu Pro Asn Asn Thr Ala Ser Trp Phe Thr
1               5                   10                  15

<210> SEQ ID NO 23
<211> LENGTH: 18
<212> TYPE: PRT
<213> ORGANISM: Severe acute respiratory syndrome coronavirus 2

<400> SEQUENCE: 23

Gly Leu Pro Asn Asn Thr Ala Ser Trp Phe Thr Ala Leu Thr Gln His
1               5                   10                  15

Gly Lys

<210> SEQ ID NO 24
<211> LENGTH: 17
<212> TYPE: PRT
<213> ORGANISM: Severe acute respiratory syndrome coronavirus 2

<400> SEQUENCE: 24

Ile Arg Gln Gly Thr Asp Tyr Lys His Trp Pro Gln Ile Ala Gln Phe
1               5                   10                  15

Ala

<210> SEQ ID NO 25
<211> LENGTH: 17
<212> TYPE: PRT
<213> ORGANISM: Severe acute respiratory syndrome coronavirus 2

<400> SEQUENCE: 25

Lys His Trp Pro Gln Ile Ala Gln Phe Ala Pro Ser Ala Ser Ala Phe
1               5                   10                  15

Phe

<210> SEQ ID NO 26
<211> LENGTH: 8
<212> TYPE: PRT
<213> ORGANISM: Severe acute respiratory syndrome coronavirus 2

<400> SEQUENCE: 26

Gln Gly Thr Asp Tyr Lys His Trp
1               5

<210> SEQ ID NO 27
<211> LENGTH: 6
<212> TYPE: PRT
<213> ORGANISM: Severe acute respiratory syndrome coronavirus 2

<400> SEQUENCE: 27
```

Leu Leu Pro Ala Ala Asp
1               5

<210> SEQ ID NO 28
<211> LENGTH: 9
<212> TYPE: PRT
<213> ORGANISM: Severe acute respiratory syndrome coronavirus 2

<400> SEQUENCE: 28

Tyr Thr Asn Ser Phe Thr Arg Gly Val
1               5

<210> SEQ ID NO 29
<211> LENGTH: 9
<212> TYPE: PRT
<213> ORGANISM: Severe acute respiratory syndrome coronavirus 2

<400> SEQUENCE: 29

Ser Thr Gln Asp Leu Phe Leu Pro Phe
1               5

<210> SEQ ID NO 30
<211> LENGTH: 9
<212> TYPE: PRT
<213> ORGANISM: Severe acute respiratory syndrome coronavirus 2

<400> SEQUENCE: 30

Arg Phe Asp Asn Pro Val Leu Pro Phe
1               5

<210> SEQ ID NO 31
<211> LENGTH: 9
<212> TYPE: PRT
<213> ORGANISM: Severe acute respiratory syndrome coronavirus 2

<400> SEQUENCE: 31

Ile Val Asn Asn Ala Thr Asn Val Val
1               5

<210> SEQ ID NO 32
<211> LENGTH: 9
<212> TYPE: PRT
<213> ORGANISM: Severe acute respiratory syndrome coronavirus 2

<400> SEQUENCE: 32

Tyr Leu Gln Pro Arg Thr Phe Leu Leu
1               5

<210> SEQ ID NO 33
<211> LENGTH: 9
<212> TYPE: PRT
<213> ORGANISM: Severe acute respiratory syndrome coronavirus 2

<400> SEQUENCE: 33

Asn Val Tyr Ala Asp Ser Phe Val Ile
1               5

<210> SEQ ID NO 34
<211> LENGTH: 9
<212> TYPE: PRT
<213> ORGANISM: Severe acute respiratory syndrome coronavirus 2

<400> SEQUENCE: 34

Ser Ile Ile Ala Tyr Thr Met Ser Leu

```
<210> SEQ ID NO 35
<211> LENGTH: 9
<212> TYPE: PRT
<213> ORGANISM: Severe acute respiratory syndrome coronavirus 2

<400> SEQUENCE: 35

Phe Thr Ile Ser Val Thr Thr Glu Ile
1               5

<210> SEQ ID NO 36
<211> LENGTH: 9
<212> TYPE: PRT
<213> ORGANISM: Severe acute respiratory syndrome coronavirus 2

<400> SEQUENCE: 36

Phe Ala Met Gln Met Ala Tyr Arg Phe
1               5

<210> SEQ ID NO 37
<211> LENGTH: 9
<212> TYPE: PRT
<213> ORGANISM: Severe acute respiratory syndrome coronavirus 2

<400> SEQUENCE: 37

Phe Val Ser Asn Gly Thr His Trp Phe
1               5

<210> SEQ ID NO 38
<211> LENGTH: 9
<212> TYPE: PRT
<213> ORGANISM: Severe acute respiratory syndrome coronavirus 2

<400> SEQUENCE: 38

Asn Thr Ala Ser Trp Phe Thr Ala Leu
1               5

<210> SEQ ID NO 39
<211> LENGTH: 9
<212> TYPE: PRT
<213> ORGANISM: Severe acute respiratory syndrome coronavirus 2

<400> SEQUENCE: 39

Lys Ala Tyr Asn Val Thr Gln Ala Phe
1               5

<210> SEQ ID NO 40
<211> LENGTH: 9
<212> TYPE: PRT
<213> ORGANISM: Severe acute respiratory syndrome coronavirus 2

<400> SEQUENCE: 40

Phe Ala Pro Ser Ala Ser Ala Phe Phe
1               5

<210> SEQ ID NO 41
<211> LENGTH: 9
<212> TYPE: PRT
<213> ORGANISM: Severe acute respiratory syndrome coronavirus 2

<400> SEQUENCE: 41

Phe Ser Lys Gln Leu Gln Gln Ser Met
1               5
```

<210> SEQ ID NO 42
<211> LENGTH: 9
<212> TYPE: PRT
<213> ORGANISM: Severe acute respiratory syndrome coronavirus 2

<400> SEQUENCE: 42

Arg Leu Phe Ala Arg Thr Arg Ser Met
1               5

<210> SEQ ID NO 43
<211> LENGTH: 9
<212> TYPE: PRT
<213> ORGANISM: Severe acute respiratory syndrome coronavirus 2

<400> SEQUENCE: 43

Tyr Val Tyr Ser Arg Val Lys Asn Leu
1               5

<210> SEQ ID NO 44
<211> LENGTH: 15
<212> TYPE: PRT
<213> ORGANISM: Severe acute respiratory syndrome coronavirus 2

<400> SEQUENCE: 44

Tyr Tyr Pro Asp Lys Val Phe Arg Ser Ser Val Leu His Ser Thr
1               5                   10                  15

<210> SEQ ID NO 45
<211> LENGTH: 15
<212> TYPE: PRT
<213> ORGANISM: Severe acute respiratory syndrome coronavirus 2

<400> SEQUENCE: 45

Ser Thr Gln Asp Leu Phe Leu Pro Phe Phe Ser Asn Val Thr Trp
1               5                   10                  15

<210> SEQ ID NO 46
<211> LENGTH: 15
<212> TYPE: PRT
<213> ORGANISM: Severe acute respiratory syndrome coronavirus 2

<400> SEQUENCE: 46

Asp Gly Val Tyr Phe Ala Ser Thr Glu Lys Ser Asn Ile Ile Arg
1               5                   10                  15

<210> SEQ ID NO 47
<211> LENGTH: 15
<212> TYPE: PRT
<213> ORGANISM: Severe acute respiratory syndrome coronavirus 2

<400> SEQUENCE: 47

Lys Thr Gln Ser Leu Leu Ile Val Asn Asn Ala Thr Asn Val Val
1               5                   10                  15

<210> SEQ ID NO 48
<211> LENGTH: 15
<212> TYPE: PRT
<213> ORGANISM: Severe acute respiratory syndrome coronavirus 2

<400> SEQUENCE: 48

Ala Ala Ala Tyr Tyr Val Gly Tyr Leu Gln Pro Arg Thr Phe Leu
1               5                   10                  15

<210> SEQ ID NO 49

-continued

```
<211> LENGTH: 15
<212> TYPE: PRT
<213> ORGANISM: Severe acute respiratory syndrome coronavirus 2

<400> SEQUENCE: 49

Cys Phe Thr Asn Val Tyr Ala Asp Ser Phe Val Ile Arg Gly Asp
1               5                   10                  15

<210> SEQ ID NO 50
<211> LENGTH: 15
<212> TYPE: PRT
<213> ORGANISM: Severe acute respiratory syndrome coronavirus 2

<400> SEQUENCE: 50

Ser Gln Ser Ile Ile Ala Tyr Thr Met Ser Leu Gly Ala Glu Asn
1               5                   10                  15

<210> SEQ ID NO 51
<211> LENGTH: 15
<212> TYPE: PRT
<213> ORGANISM: Severe acute respiratory syndrome coronavirus 2

<400> SEQUENCE: 51

Thr Asn Phe Thr Ile Ser Val Thr Thr Glu Ile Leu Pro Val Ser
1               5                   10                  15

<210> SEQ ID NO 52
<211> LENGTH: 15
<212> TYPE: PRT
<213> ORGANISM: Severe acute respiratory syndrome coronavirus 2

<400> SEQUENCE: 52

Ala Leu Gln Ile Pro Phe Ala Met Gln Met Ala Tyr Arg Phe Asn
1               5                   10                  15

<210> SEQ ID NO 53
<211> LENGTH: 15
<212> TYPE: PRT
<213> ORGANISM: Severe acute respiratory syndrome coronavirus 2

<400> SEQUENCE: 53

Phe Ala Met Gln Met Ala Tyr Arg Phe Asn Gly Ile Gly Val Thr
1               5                   10                  15

<210> SEQ ID NO 54
<211> LENGTH: 15
<212> TYPE: PRT
<213> ORGANISM: Severe acute respiratory syndrome coronavirus 2

<400> SEQUENCE: 54

His Trp Phe Val Thr Gln Arg Asn Phe Tyr Glu Pro Gln Ile Ile
1               5                   10                  15

<210> SEQ ID NO 55
<211> LENGTH: 15
<212> TYPE: PRT
<213> ORGANISM: Severe acute respiratory syndrome coronavirus 2

<400> SEQUENCE: 55

Asn Asn Thr Ala Ser Trp Phe Thr Ala Leu Thr Gln His Gly Lys
1               5                   10                  15

<210> SEQ ID NO 56
<211> LENGTH: 15
<212> TYPE: PRT
```

<213> ORGANISM: Severe acute respiratory syndrome coronavirus 2

<400> SEQUENCE: 56

Thr Ala Thr Lys Ala Tyr Asn Val Thr Gln Ala Phe Gly Arg Arg
1               5                   10                  15

<210> SEQ ID NO 57
<211> LENGTH: 15
<212> TYPE: PRT
<213> ORGANISM: Severe acute respiratory syndrome coronavirus 2

<400> SEQUENCE: 57

Gln Ile Ala Gln Phe Ala Pro Ser Ala Ser Ala Phe Phe Gly Met
1               5                   10                  15

<210> SEQ ID NO 58
<211> LENGTH: 15
<212> TYPE: PRT
<213> ORGANISM: Severe acute respiratory syndrome coronavirus 2

<400> SEQUENCE: 58

Lys Lys Gln Gln Thr Val Thr Leu Leu Pro Ala Ala Asp Leu Asp
1               5                   10                  15

<210> SEQ ID NO 59
<211> LENGTH: 15
<212> TYPE: PRT
<213> ORGANISM: Severe acute respiratory syndrome coronavirus 2

<400> SEQUENCE: 59

Leu Ser Tyr Phe Ile Ala Ser Phe Arg Leu Phe Ala Arg Thr Arg
1               5                   10                  15

<210> SEQ ID NO 60
<211> LENGTH: 15
<212> TYPE: PRT
<213> ORGANISM: Severe acute respiratory syndrome coronavirus 2

<400> SEQUENCE: 60

Lys Pro Ser Phe Tyr Val Tyr Ser Arg Val Lys Asn Leu Asn Ser
1               5                   10                  15

<210> SEQ ID NO 61
<211> LENGTH: 9
<212> TYPE: PRT
<213> ORGANISM: Severe acute respiratory syndrome coronavirus

<400> SEQUENCE: 61

Phe Ile Ala Gly Leu Ile Ala Ile Val
1               5

<210> SEQ ID NO 62
<211> LENGTH: 10
<212> TYPE: PRT
<213> ORGANISM: Severe acute respiratory syndrome coronavirus

<400> SEQUENCE: 62

Gly Leu Ile Ala Ile Val Met Val Thr Ile
1               5                   10

<210> SEQ ID NO 63
<211> LENGTH: 9
<212> TYPE: PRT
<213> ORGANISM: Severe acute respiratory syndrome coronavirus

```
<400> SEQUENCE: 63

Ile Ile Thr Thr Asp Asn Thr Phe Val
1               5

<210> SEQ ID NO 64
<211> LENGTH: 9
<212> TYPE: PRT
<213> ORGANISM: Severe acute respiratory syndrome coronavirus

<400> SEQUENCE: 64

Ala Leu Asn Thr Leu Val Lys Gln Leu
1               5

<210> SEQ ID NO 65
<211> LENGTH: 9
<212> TYPE: PRT
<213> ORGANISM: Severe acute respiratory syndrome coronavirus

<400> SEQUENCE: 65

Leu Ile Thr Gly Arg Leu Gln Ser Leu
1               5

<210> SEQ ID NO 66
<211> LENGTH: 9
<212> TYPE: PRT
<213> ORGANISM: Severe acute respiratory syndrome coronavirus

<400> SEQUENCE: 66

Leu Leu Leu Gln Tyr Gly Ser Phe Cys
1               5

<210> SEQ ID NO 67
<211> LENGTH: 8
<212> TYPE: PRT
<213> ORGANISM: Severe acute respiratory syndrome coronavirus

<400> SEQUENCE: 67

Leu Gln Tyr Gly Ser Phe Cys Thr
1               5

<210> SEQ ID NO 68
<211> LENGTH: 9
<212> TYPE: PRT
<213> ORGANISM: Severe acute respiratory syndrome coronavirus

<400> SEQUENCE: 68

Asn Leu Asn Glu Ser Leu Ile Asp Leu
1               5

<210> SEQ ID NO 69
<211> LENGTH: 9
<212> TYPE: PRT
<213> ORGANISM: Severe acute respiratory syndrome coronavirus

<400> SEQUENCE: 69

Arg Leu Asp Lys Val Glu Ala Glu Val
1               5

<210> SEQ ID NO 70
<211> LENGTH: 9
<212> TYPE: PRT
<213> ORGANISM: Severe acute respiratory syndrome coronavirus

<400> SEQUENCE: 70
```

Arg Leu Asn Glu Val Ala Lys Asn Leu
1               5

<210> SEQ ID NO 71
<211> LENGTH: 9
<212> TYPE: PRT
<213> ORGANISM: Severe acute respiratory syndrome coronavirus

<400> SEQUENCE: 71

Arg Leu Gln Ser Leu Gln Thr Tyr Val
1               5

<210> SEQ ID NO 72
<211> LENGTH: 9
<212> TYPE: PRT
<213> ORGANISM: Severe acute respiratory syndrome coronavirus

<400> SEQUENCE: 72

Val Leu Asn Asp Ile Leu Ser Arg Leu
1               5

<210> SEQ ID NO 73
<211> LENGTH: 9
<212> TYPE: PRT
<213> ORGANISM: Severe acute respiratory syndrome coronavirus

<400> SEQUENCE: 73

Val Val Phe Leu His Val Thr Tyr Val
1               5

<210> SEQ ID NO 74
<211> LENGTH: 8
<212> TYPE: PRT
<213> ORGANISM: Severe acute respiratory syndrome coronavirus

<400> SEQUENCE: 74

Ile Leu Leu Asn Lys His Ile Asp
1               5

<210> SEQ ID NO 75
<211> LENGTH: 9
<212> TYPE: PRT
<213> ORGANISM: Severe acute respiratory syndrome coronavirus

<400> SEQUENCE: 75

Phe Pro Arg Gly Gln Gly Val Pro Ile
1               5

<210> SEQ ID NO 76
<211> LENGTH: 9
<212> TYPE: PRT
<213> ORGANISM: Severe acute respiratory syndrome coronavirus

<400> SEQUENCE: 76

Leu Leu Leu Leu Asp Arg Leu Asn Gln
1               5

<210> SEQ ID NO 77
<211> LENGTH: 9
<212> TYPE: PRT
<213> ORGANISM: Severe acute respiratory syndrome coronavirus

<400> SEQUENCE: 77

Gly Met Ser Arg Ile Gly Met Glu Val
1               5

```
<210> SEQ ID NO 78
<211> LENGTH: 9
<212> TYPE: PRT
<213> ORGANISM: Severe acute respiratory syndrome coronavirus

<400> SEQUENCE: 78

Ile Leu Leu Asn Lys His Ile Asp Ala
1               5

<210> SEQ ID NO 79
<211> LENGTH: 9
<212> TYPE: PRT
<213> ORGANISM: Severe acute respiratory syndrome coronavirus

<400> SEQUENCE: 79

Ala Leu Asn Thr Pro Lys Asp His Ile
1               5

<210> SEQ ID NO 80
<211> LENGTH: 9
<212> TYPE: PRT
<213> ORGANISM: Severe acute respiratory syndrome coronavirus

<400> SEQUENCE: 80

Leu Ala Leu Leu Leu Leu Asp Arg Leu
1               5

<210> SEQ ID NO 81
<211> LENGTH: 9
<212> TYPE: PRT
<213> ORGANISM: Severe acute respiratory syndrome coronavirus

<400> SEQUENCE: 81

Leu Leu Leu Asp Arg Leu Asn Gln Leu
1               5

<210> SEQ ID NO 82
<211> LENGTH: 10
<212> TYPE: PRT
<213> ORGANISM: Severe acute respiratory syndrome coronavirus

<400> SEQUENCE: 82

Leu Leu Leu Leu Asp Arg Leu Asn Gln Leu
1               5                   10

<210> SEQ ID NO 83
<211> LENGTH: 9
<212> TYPE: PRT
<213> ORGANISM: Severe acute respiratory syndrome coronavirus

<400> SEQUENCE: 83

Leu Gln Leu Pro Gln Gly Thr Thr Leu
1               5

<210> SEQ ID NO 84
<211> LENGTH: 9
<212> TYPE: PRT
<213> ORGANISM: Severe acute respiratory syndrome coronavirus

<400> SEQUENCE: 84

Ala Gln Phe Ala Pro Ser Ala Ser Ala
1               5
```

```
<210> SEQ ID NO 85
<211> LENGTH: 9
<212> TYPE: PRT
<213> ORGANISM: Severe acute respiratory syndrome coronavirus

<400> SEQUENCE: 85

Thr Thr Leu Pro Lys Gly Phe Tyr Ala
1               5

<210> SEQ ID NO 86
<211> LENGTH: 10
<212> TYPE: PRT
<213> ORGANISM: Severe acute respiratory syndrome coronavirus

<400> SEQUENCE: 86

Val Leu Gln Leu Pro Gln Gly Thr Thr Leu
1               5                   10

<210> SEQ ID NO 87
<211> LENGTH: 10
<212> TYPE: PRT
<213> ORGANISM: Severe acute respiratory syndrome coronavirus

<400> SEQUENCE: 87

Gly Tyr Gln Pro Tyr Arg Val Val Val Leu
1               5                   10

<210> SEQ ID NO 88
<211> LENGTH: 9
<212> TYPE: PRT
<213> ORGANISM: Severe acute respiratory syndrome coronavirus

<400> SEQUENCE: 88

Pro Tyr Arg Val Val Val Leu Ser Phe
1               5

<210> SEQ ID NO 89
<211> LENGTH: 9
<212> TYPE: PRT
<213> ORGANISM: Severe acute respiratory syndrome coronavirus

<400> SEQUENCE: 89

Leu Ser Pro Arg Trp Tyr Phe Tyr Tyr
1               5

<210> SEQ ID NO 90
<211> LENGTH: 10
<212> TYPE: PRT
<213> ORGANISM: Severe acute respiratory syndrome coronavirus

<400> SEQUENCE: 90

Asp Ser Phe Lys Glu Glu Leu Asp Lys Tyr
1               5                   10

<210> SEQ ID NO 91
<211> LENGTH: 10
<212> TYPE: PRT
<213> ORGANISM: Severe acute respiratory syndrome coronavirus

<400> SEQUENCE: 91

Leu Ile Asp Leu Gln Glu Leu Gly Lys Tyr
1               5                   10

<210> SEQ ID NO 92
<211> LENGTH: 9
```

<212> TYPE: PRT
<213> ORGANISM: Severe acute respiratory syndrome coronavirus

<400> SEQUENCE: 92

Gly Thr Thr Leu Pro Lys Gly Phe Tyr
1               5

<210> SEQ ID NO 93
<211> LENGTH: 10
<212> TYPE: PRT
<213> ORGANISM: Severe acute respiratory syndrome coronavirus

<400> SEQUENCE: 93

Val Thr Pro Ser Gly Thr Trp Leu Thr Tyr
1               5                   10

<210> SEQ ID NO 94
<211> LENGTH: 9
<212> TYPE: PRT
<213> ORGANISM: Severe acute respiratory syndrome coronavirus

<400> SEQUENCE: 94

Gly Ser Phe Cys Thr Gln Leu Asn Arg
1               5

<210> SEQ ID NO 95
<211> LENGTH: 9
<212> TYPE: PRT
<213> ORGANISM: Severe acute respiratory syndrome coronavirus

<400> SEQUENCE: 95

Gly Val Val Phe Leu His Val Thr Tyr
1               5

<210> SEQ ID NO 96
<211> LENGTH: 9
<212> TYPE: PRT
<213> ORGANISM: Severe acute respiratory syndrome coronavirus

<400> SEQUENCE: 96

Ala Gln Ala Leu Asn Thr Leu Val Lys
1               5

<210> SEQ ID NO 97
<211> LENGTH: 9
<212> TYPE: PRT
<213> ORGANISM: Severe acute respiratory syndrome coronavirus

<400> SEQUENCE: 97

Met Thr Ser Cys Cys Ser Cys Leu Lys
1               5

<210> SEQ ID NO 98
<211> LENGTH: 9
<212> TYPE: PRT
<213> ORGANISM: Severe acute respiratory syndrome coronavirus

<400> SEQUENCE: 98

Ala Ser Ala Asn Leu Ala Ala Thr Lys
1               5

<210> SEQ ID NO 99
<211> LENGTH: 10
<212> TYPE: PRT
<213> ORGANISM: Severe acute respiratory syndrome coronavirus

```
<400> SEQUENCE: 99

Ser Leu Ile Asp Leu Gln Glu Leu Gly Lys
1               5                   10

<210> SEQ ID NO 100
<211> LENGTH: 9
<212> TYPE: PRT
<213> ORGANISM: Severe acute respiratory syndrome coronavirus

<400> SEQUENCE: 100

Ser Val Leu Asn Asp Ile Leu Ser Arg
1               5

<210> SEQ ID NO 101
<211> LENGTH: 10
<212> TYPE: PRT
<213> ORGANISM: Severe acute respiratory syndrome coronavirus

<400> SEQUENCE: 101

Thr Gln Asn Val Leu Tyr Glu Asn Gln Lys
1               5                   10

<210> SEQ ID NO 102
<211> LENGTH: 10
<212> TYPE: PRT
<213> ORGANISM: Severe acute respiratory syndrome coronavirus

<400> SEQUENCE: 102

Cys Met Thr Ser Cys Cys Ser Cys Leu Lys
1               5                   10

<210> SEQ ID NO 103
<211> LENGTH: 10
<212> TYPE: PRT
<213> ORGANISM: Severe acute respiratory syndrome coronavirus

<400> SEQUENCE: 103

Val Gln Ile Asp Arg Leu Ile Thr Gly Arg
1               5                   10

<210> SEQ ID NO 104
<211> LENGTH: 9
<212> TYPE: PRT
<213> ORGANISM: Severe acute respiratory syndrome coronavirus

<400> SEQUENCE: 104

Lys Thr Phe Pro Pro Thr Glu Pro Lys
1               5

<210> SEQ ID NO 105
<211> LENGTH: 10
<212> TYPE: PRT
<213> ORGANISM: Severe acute respiratory syndrome coronavirus

<400> SEQUENCE: 105

Lys Thr Phe Pro Pro Thr Glu Pro Lys Lys
1               5                   10

<210> SEQ ID NO 106
<211> LENGTH: 9
<212> TYPE: PRT
<213> ORGANISM: Severe acute respiratory syndrome coronavirus

<400> SEQUENCE: 106
```

```
Ala Ser Ala Phe Phe Gly Met Ser Arg
1               5
```

<210> SEQ ID NO 107
<211> LENGTH: 10
<212> TYPE: PRT
<213> ORGANISM: Severe acute respiratory syndrome coronavirus

<400> SEQUENCE: 107

```
Ala Thr Glu Gly Ala Leu Asn Thr Pro Lys
1               5                   10
```

<210> SEQ ID NO 108
<211> LENGTH: 10
<212> TYPE: PRT
<213> ORGANISM: Severe acute respiratory syndrome coronavirus

<400> SEQUENCE: 108

```
Gln Leu Pro Gln Gly Thr Thr Leu Pro Lys
1               5                   10
```

<210> SEQ ID NO 109
<211> LENGTH: 9
<212> TYPE: PRT
<213> ORGANISM: Severe acute respiratory syndrome coronavirus

<400> SEQUENCE: 109

```
Gln Gln Gln Gly Gln Thr Val Thr Lys
1               5
```

<210> SEQ ID NO 110
<211> LENGTH: 10
<212> TYPE: PRT
<213> ORGANISM: Severe acute respiratory syndrome coronavirus

<400> SEQUENCE: 110

```
Gln Gln Gln Gln Gly Gln Thr Val Thr Lys
1               5                   10
```

<210> SEQ ID NO 111
<211> LENGTH: 10
<212> TYPE: PRT
<213> ORGANISM: Severe acute respiratory syndrome coronavirus

<400> SEQUENCE: 111

```
Ser Ala Ser Ala Phe Phe Gly Met Ser Arg
1               5                   10
```

<210> SEQ ID NO 112
<211> LENGTH: 10
<212> TYPE: PRT
<213> ORGANISM: Severe acute respiratory syndrome coronavirus

<400> SEQUENCE: 112

```
Ser Gln Ala Ser Ser Arg Ser Ser Ser Arg
1               5                   10
```

<210> SEQ ID NO 113
<211> LENGTH: 9
<212> TYPE: PRT
<213> ORGANISM: Severe acute respiratory syndrome coronavirus

<400> SEQUENCE: 113

```
Thr Pro Ser Gly Thr Trp Leu Thr Tyr
```

```
<210> SEQ ID NO 114
<211> LENGTH: 10
<212> TYPE: PRT
<213> ORGANISM: Severe acute respiratory syndrome coronavirus

<400> SEQUENCE: 114

Phe Pro Asn Ile Thr Asn Leu Cys Pro Phe
1               5                   10

<210> SEQ ID NO 115
<211> LENGTH: 10
<212> TYPE: PRT
<213> ORGANISM: Severe acute respiratory syndrome coronavirus

<400> SEQUENCE: 115

Ala Pro His Gly Val Val Phe Leu His Val
1               5                   10

<210> SEQ ID NO 116
<211> LENGTH: 10
<212> TYPE: PRT
<213> ORGANISM: Severe acute respiratory syndrome coronavirus

<400> SEQUENCE: 116

Ala Pro Ser Ala Ser Ala Phe Phe Gly Met
1               5                   10

<210> SEQ ID NO 117
<211> LENGTH: 9
<212> TYPE: PRT
<213> ORGANISM: Severe acute respiratory syndrome coronavirus

<400> SEQUENCE: 117

Leu Gln Ile Pro Phe Ala Met Gln Met
1               5

<210> SEQ ID NO 118
<211> LENGTH: 9
<212> TYPE: PRT
<213> ORGANISM: Severe acute respiratory syndrome coronavirus

<400> SEQUENCE: 118

Arg Val Asp Phe Cys Gly Lys Gly Tyr
1               5

<210> SEQ ID NO 119
<211> LENGTH: 10
<212> TYPE: PRT
<213> ORGANISM: Severe acute respiratory syndrome coronavirus

<400> SEQUENCE: 119

Tyr Glu Gln Tyr Ile Lys Trp Pro Trp Tyr
1               5                   10

<210> SEQ ID NO 120
<211> LENGTH: 9
<212> TYPE: PRT
<213> ORGANISM: Severe acute respiratory syndrome coronavirus

<400> SEQUENCE: 120

Gly Arg Leu Gln Ser Leu Gln Thr Tyr
1               5
```

```
<210> SEQ ID NO 121
<211> LENGTH: 9
<212> TYPE: PRT
<213> ORGANISM: Severe acute respiratory syndrome coronavirus

<400> SEQUENCE: 121

Val Arg Phe Pro Asn Ile Thr Asn Leu
1               5

<210> SEQ ID NO 122
<211> LENGTH: 1273
<212> TYPE: PRT
<213> ORGANISM: Severe acute respiratory syndrome coronavirus 2

<400> SEQUENCE: 122

Met Phe Val Phe Leu Val Leu Leu Pro Leu Val Ser Ser Gln Cys Val
1               5                   10                  15

Asn Leu Thr Thr Arg Thr Gln Leu Pro Pro Ala Tyr Thr Asn Ser Phe
            20                  25                  30

Thr Arg Gly Val Tyr Tyr Pro Asp Lys Val Phe Arg Ser Ser Val Leu
        35                  40                  45

His Ser Thr Gln Asp Leu Phe Leu Pro Phe Phe Ser Asn Val Thr Trp
    50                  55                  60

Phe His Ala Ile His Val Ser Gly Thr Asn Gly Thr Lys Arg Phe Asp
65                  70                  75                  80

Asn Pro Val Leu Pro Phe Asn Asp Gly Val Tyr Phe Ala Ser Thr Glu
                85                  90                  95

Lys Ser Asn Ile Ile Arg Gly Trp Ile Phe Gly Thr Thr Leu Asp Ser
            100                 105                 110

Lys Thr Gln Ser Leu Leu Ile Val Asn Asn Ala Thr Asn Val Val Ile
        115                 120                 125

Lys Val Cys Glu Phe Gln Phe Cys Asn Asp Pro Phe Leu Gly Val Tyr
    130                 135                 140

Tyr His Lys Asn Asn Lys Ser Trp Met Glu Ser Glu Phe Arg Val Tyr
145                 150                 155                 160

Ser Ser Ala Asn Asn Cys Thr Phe Glu Tyr Val Ser Gln Pro Phe Leu
                165                 170                 175

Met Asp Leu Glu Gly Lys Gln Gly Asn Phe Lys Asn Leu Arg Glu Phe
            180                 185                 190

Val Phe Lys Asn Ile Asp Gly Tyr Phe Lys Ile Tyr Ser Lys His Thr
        195                 200                 205

Pro Ile Asn Leu Val Arg Asp Leu Pro Gln Gly Phe Ser Ala Leu Glu
    210                 215                 220

Pro Leu Val Asp Leu Pro Ile Gly Ile Asn Ile Thr Arg Phe Gln Thr
225                 230                 235                 240

Leu Leu Ala Leu His Arg Ser Tyr Leu Thr Pro Gly Asp Ser Ser Ser
                245                 250                 255

Gly Trp Thr Ala Gly Ala Ala Ala Tyr Tyr Val Gly Tyr Leu Gln Pro
            260                 265                 270

Arg Thr Phe Leu Leu Lys Tyr Asn Glu Asn Gly Thr Ile Thr Asp Ala
        275                 280                 285

Val Asp Cys Ala Leu Asp Pro Leu Ser Glu Thr Lys Cys Thr Leu Lys
    290                 295                 300

Ser Phe Thr Val Glu Lys Gly Ile Tyr Gln Thr Ser Asn Phe Arg Val
305                 310                 315                 320
```

```
Gln Pro Thr Glu Ser Ile Val Arg Phe Pro Asn Ile Thr Asn Leu Cys
            325                 330                 335

Pro Phe Gly Glu Val Phe Asn Ala Thr Arg Phe Ala Ser Val Tyr Ala
            340                 345                 350

Trp Asn Arg Lys Arg Ile Ser Asn Cys Val Ala Asp Tyr Ser Val Leu
            355                 360                 365

Tyr Asn Ser Ala Ser Phe Ser Thr Phe Lys Cys Tyr Gly Val Ser Pro
        370                 375                 380

Thr Lys Leu Asn Asp Leu Cys Phe Thr Asn Val Tyr Ala Asp Ser Phe
385                 390                 395                 400

Val Ile Arg Gly Asp Glu Val Arg Gln Ile Ala Pro Gly Gln Thr Gly
                405                 410                 415

Lys Ile Ala Asp Tyr Asn Tyr Lys Leu Pro Asp Asp Phe Thr Gly Cys
            420                 425                 430

Val Ile Ala Trp Asn Ser Asn Asn Leu Asp Ser Lys Val Gly Gly Asn
            435                 440                 445

Tyr Asn Tyr Leu Tyr Arg Leu Phe Arg Lys Ser Asn Leu Lys Pro Phe
        450                 455                 460

Glu Arg Asp Ile Ser Thr Glu Ile Tyr Gln Ala Gly Ser Thr Pro Cys
465                 470                 475                 480

Asn Gly Val Glu Gly Phe Asn Cys Tyr Phe Pro Leu Gln Ser Tyr Gly
                485                 490                 495

Phe Gln Pro Thr Asn Gly Val Gly Tyr Gln Pro Tyr Arg Val Val Val
            500                 505                 510

Leu Ser Phe Glu Leu Leu His Ala Pro Ala Thr Val Cys Gly Pro Lys
        515                 520                 525

Lys Ser Thr Asn Leu Val Lys Asn Lys Cys Val Asn Phe Asn Phe Asn
530                 535                 540

Gly Leu Thr Gly Thr Gly Val Leu Thr Glu Ser Asn Lys Lys Phe Leu
545                 550                 555                 560

Pro Phe Gln Gln Phe Gly Arg Asp Ile Ala Thr Thr Asp Ala Val
            565                 570                 575

Arg Asp Pro Gln Thr Leu Glu Ile Leu Asp Ile Thr Pro Cys Ser Phe
            580                 585                 590

Gly Gly Val Ser Val Ile Thr Pro Gly Thr Asn Thr Ser Asn Gln Val
        595                 600                 605

Ala Val Leu Tyr Gln Asp Val Asn Cys Thr Glu Val Pro Val Ala Ile
        610                 615                 620

His Ala Asp Gln Leu Thr Pro Thr Trp Arg Val Tyr Ser Thr Gly Ser
625                 630                 635                 640

Asn Val Phe Gln Thr Arg Ala Gly Cys Leu Ile Gly Ala Glu His Val
            645                 650                 655

Asn Asn Ser Tyr Glu Cys Asp Ile Pro Ile Gly Ala Gly Ile Cys Ala
            660                 665                 670

Ser Tyr Gln Thr Gln Thr Asn Ser Pro Arg Arg Ala Arg Ser Val Ala
        675                 680                 685

Ser Gln Ser Ile Ile Ala Tyr Thr Met Ser Leu Gly Ala Glu Asn Ser
    690                 695                 700

Val Ala Tyr Ser Asn Asn Ser Ile Ala Ile Pro Thr Asn Phe Thr Ile
705                 710                 715                 720

Ser Val Thr Thr Glu Ile Leu Pro Val Ser Met Thr Lys Thr Ser Val
                725                 730                 735

Asp Cys Thr Met Tyr Ile Cys Gly Asp Ser Thr Glu Cys Ser Asn Leu
```

-continued

```
                740             745             750
Leu Leu Gln Tyr Gly Ser Phe Cys Thr Gln Leu Asn Arg Ala Leu Thr
                    755             760             765
Gly Ile Ala Val Glu Gln Asp Lys Asn Thr Gln Glu Val Phe Ala Gln
                770             775             780
Val Lys Gln Ile Tyr Lys Thr Pro Pro Ile Lys Asp Phe Gly Gly Phe
785             790             795             800
Asn Phe Ser Gln Ile Leu Pro Asp Pro Ser Lys Pro Ser Lys Arg Ser
                    805             810             815
Phe Ile Glu Asp Leu Leu Phe Asn Lys Val Thr Leu Ala Asp Ala Gly
                820             825             830
Phe Ile Lys Gln Tyr Gly Asp Cys Leu Gly Asp Ile Ala Ala Arg Asp
                835             840             845
Leu Ile Cys Ala Gln Lys Phe Asn Gly Leu Thr Val Leu Pro Pro Leu
                850             855             860
Leu Thr Asp Glu Met Ile Ala Gln Tyr Thr Ser Ala Leu Leu Ala Gly
865             870             875             880
Thr Ile Thr Ser Gly Trp Thr Phe Gly Ala Gly Ala Ala Leu Gln Ile
                    885             890             895
Pro Phe Ala Met Gln Met Ala Tyr Arg Phe Asn Gly Ile Gly Val Thr
                900             905             910
Gln Asn Val Leu Tyr Glu Asn Gln Lys Leu Ile Ala Asn Gln Phe Asn
                    915             920             925
Ser Ala Ile Gly Lys Ile Gln Asp Ser Leu Ser Ser Thr Ala Ser Ala
                930             935             940
Leu Gly Lys Leu Gln Asp Val Val Asn Gln Asn Ala Gln Ala Leu Asn
945             950             955             960
Thr Leu Val Lys Gln Leu Ser Ser Asn Phe Gly Ala Ile Ser Ser Val
                    965             970             975
Leu Asn Asp Ile Leu Ser Arg Leu Asp Lys Val Glu Ala Glu Val Gln
                    980             985             990
Ile Asp Arg Leu Ile Thr Gly Arg Leu Gln Ser Leu Gln Thr Tyr Val
                995             1000            1005
Thr Gln Gln Leu Ile Arg Ala Ala Glu Ile Arg Ala Ser Ala Asn
                1010            1015            1020
Leu Ala Ala Thr Lys Met Ser Glu Cys Val Leu Gly Gln Ser Lys
                1025            1030            1035
Arg Val Asp Phe Cys Gly Lys Gly Tyr His Leu Met Ser Phe Pro
                1040            1045            1050
Gln Ser Ala Pro His Gly Val Val Phe Leu His Val Thr Tyr Val
                1055            1060            1065
Pro Ala Gln Glu Lys Asn Phe Thr Thr Ala Pro Ala Ile Cys His
                1070            1075            1080
Asp Gly Lys Ala His Phe Pro Arg Glu Gly Val Phe Val Ser Asn
                1085            1090            1095
Gly Thr His Trp Phe Val Thr Gln Arg Asn Phe Tyr Glu Pro Gln
                1100            1105            1110
Ile Ile Thr Thr Asp Asn Thr Phe Val Ser Gly Asn Cys Asp Val
                1115            1120            1125
Val Ile Gly Ile Val Asn Asn Thr Val Tyr Asp Pro Leu Gln Pro
                1130            1135            1140
Glu Leu Asp Ser Phe Lys Glu Glu Leu Asp Lys Tyr Phe Lys Asn
                1145            1150            1155
```

```
His Thr Ser Pro Asp Val Asp Leu Gly Asp Ile Ser Gly Ile Asn
    1160                1165                1170

Ala Ser Val Val Asn Ile Gln Lys Glu Ile Asp Arg Leu Asn Glu
    1175                1180                1185

Val Ala Lys Asn Leu Asn Glu Ser Leu Ile Asp Leu Gln Glu Leu
    1190                1195                1200

Gly Lys Tyr Glu Gln Tyr Ile Lys Trp Pro Trp Tyr Ile Trp Leu
    1205                1210                1215

Gly Phe Ile Ala Gly Leu Ile Ala Ile Val Met Val Thr Ile Met
    1220                1225                1230

Leu Cys Cys Met Thr Ser Cys Cys Ser Cys Leu Lys Gly Cys Cys
    1235                1240                1245

Ser Cys Gly Ser Cys Cys Lys Phe Asp Glu Asp Asp Ser Glu Pro
    1250                1255                1260

Val Leu Lys Gly Val Lys Leu His Tyr Thr
    1265                1270

<210> SEQ ID NO 123
<211> LENGTH: 419
<212> TYPE: PRT
<213> ORGANISM: Severe acute respiratory syndrome coronavirus 2

<400> SEQUENCE: 123

Met Ser Asp Asn Gly Pro Gln Asn Gln Arg Asn Ala Pro Arg Ile Thr
1               5                   10                  15

Phe Gly Gly Pro Ser Asp Ser Thr Gly Ser Asn Gln Asn Gly Glu Arg
                20                  25                  30

Ser Gly Ala Arg Ser Lys Gln Arg Arg Pro Gln Gly Leu Pro Asn Asn
            35                  40                  45

Thr Ala Ser Trp Phe Thr Ala Leu Thr Gln His Gly Lys Glu Asp Leu
    50                  55                  60

Lys Phe Pro Arg Gly Gln Gly Val Pro Ile Asn Thr Asn Ser Ser Pro
65                  70                  75                  80

Asp Asp Gln Ile Gly Tyr Tyr Arg Arg Ala Thr Arg Arg Ile Arg Gly
                85                  90                  95

Gly Asp Gly Lys Met Lys Asp Leu Ser Pro Arg Trp Tyr Phe Tyr Tyr
            100                 105                 110

Leu Gly Thr Gly Pro Glu Ala Gly Leu Pro Tyr Gly Ala Asn Lys Asp
        115                 120                 125

Gly Ile Ile Trp Val Ala Thr Glu Gly Ala Leu Asn Thr Pro Lys Asp
    130                 135                 140

His Ile Gly Thr Arg Asn Pro Ala Asn Asn Ala Ala Ile Val Leu Gln
145                 150                 155                 160

Leu Pro Gln Gly Thr Thr Leu Pro Lys Gly Phe Tyr Ala Glu Gly Ser
                165                 170                 175

Arg Gly Gly Ser Gln Ala Ser Ser Arg Ser Ser Ser Arg Ser Arg Asn
            180                 185                 190

Ser Ser Arg Asn Ser Thr Pro Gly Ser Ser Arg Gly Thr Ser Pro Ala
        195                 200                 205

Arg Met Ala Gly Asn Gly Gly Asp Ala Ala Leu Ala Leu Leu Leu Leu
    210                 215                 220

Asp Arg Leu Asn Gln Leu Glu Ser Lys Met Ser Gly Lys Gly Gln Gln
225                 230                 235                 240

Gln Gln Gly Gln Thr Val Thr Lys Lys Ser Ala Ala Glu Ala Ser Lys
```

```
                    245                 250                 255
Lys Pro Arg Gln Lys Arg Thr Ala Thr Lys Ala Tyr Asn Val Thr Gln
                260                 265                 270

Ala Phe Gly Arg Arg Gly Pro Glu Gln Thr Gln Gly Asn Phe Gly Asp
            275                 280                 285

Gln Glu Leu Ile Arg Gln Gly Thr Asp Tyr Lys His Trp Pro Gln Ile
        290                 295                 300

Ala Gln Phe Ala Pro Ser Ala Ser Ala Phe Phe Gly Met Ser Arg Ile
305                 310                 315                 320

Gly Met Glu Val Thr Pro Ser Gly Thr Trp Leu Thr Tyr Thr Gly Ala
                325                 330                 335

Ile Lys Leu Asp Asp Lys Asp Pro Asn Phe Lys Asp Gln Val Ile Leu
            340                 345                 350

Leu Asn Lys His Ile Asp Ala Tyr Lys Thr Phe Pro Pro Thr Glu Pro
        355                 360                 365

Lys Lys Asp Lys Lys Lys Ala Asp Glu Thr Gln Ala Leu Pro Gln
370                 375                 380

Arg Gln Lys Lys Gln Gln Thr Val Thr Leu Leu Pro Ala Ala Asp Leu
385                 390                 395                 400

Asp Asp Phe Ser Lys Gln Leu Gln Gln Ser Met Ser Ser Ala Asp Ser
                405                 410                 415

Thr Gln Ala

<210> SEQ ID NO 124
<211> LENGTH: 75
<212> TYPE: PRT
<213> ORGANISM: Severe acute respiratory syndrome coronavirus 2

<400> SEQUENCE: 124

Met Tyr Ser Phe Val Ser Glu Glu Thr Gly Thr Leu Ile Val Asn Ser
1               5                   10                  15

Val Leu Leu Phe Leu Ala Phe Val Val Phe Leu Leu Val Thr Leu Ala
            20                  25                  30

Ile Leu Thr Ala Leu Arg Leu Cys Ala Tyr Cys Cys Asn Ile Val Asn
        35                  40                  45

Val Ser Leu Val Lys Pro Ser Phe Tyr Val Tyr Ser Arg Val Lys Asn
    50                  55                  60

Leu Asn Ser Ser Arg Val Pro Asp Leu Leu Val
65                  70                  75

<210> SEQ ID NO 125
<211> LENGTH: 222
<212> TYPE: PRT
<213> ORGANISM: Severe acute respiratory syndrome coronavirus 2

<400> SEQUENCE: 125

Met Ala Asp Ser Asn Gly Thr Ile Thr Val Glu Glu Leu Lys Lys Leu
1               5                   10                  15

Leu Glu Gln Trp Asn Leu Val Ile Gly Phe Leu Phe Leu Thr Trp Ile
            20                  25                  30

Cys Leu Leu Gln Phe Ala Tyr Ala Asn Arg Asn Arg Phe Leu Tyr Ile
        35                  40                  45

Ile Lys Leu Ile Phe Leu Trp Leu Leu Trp Pro Val Thr Leu Ala Cys
    50                  55                  60

Phe Val Leu Ala Ala Val Tyr Arg Ile Asn Trp Ile Thr Gly Gly Ile
65                  70                  75                  80
```

-continued

```
Ala Ile Ala Met Ala Cys Leu Val Gly Leu Met Trp Leu Ser Tyr Phe
            85                  90                  95

Ile Ala Ser Phe Arg Leu Phe Ala Arg Thr Arg Ser Met Trp Ser Phe
            100                 105                 110

Asn Pro Glu Thr Asn Ile Leu Leu Asn Val Pro Leu His Gly Thr Ile
        115                 120                 125

Leu Thr Arg Pro Leu Leu Glu Ser Glu Leu Val Ile Gly Ala Val Ile
        130                 135                 140

Leu Arg Gly His Leu Arg Ile Ala Gly His His Leu Gly Arg Cys Asp
145                 150                 155                 160

Ile Lys Asp Leu Pro Lys Glu Ile Thr Val Ala Thr Ser Arg Thr Leu
                165                 170                 175

Ser Tyr Tyr Lys Leu Gly Ala Ser Gln Arg Val Ala Gly Asp Ser Gly
            180                 185                 190

Phe Ala Ala Tyr Ser Arg Tyr Arg Ile Gly Asn Tyr Lys Leu Asn Thr
            195                 200                 205

Asp His Ser Ser Ser Ser Asp Asn Ile Ala Leu Leu Val Gln
210                 215                 220
```

US 10,973,909 B1

CORONAVIRUS VACCINE

CROSS-REFERENCE TO RELATED APPLICATIONS

This application claims the benefit of priority to UK Application No. 2004974.8 filed on Apr. 3, 2020, the content of which are incorporated herein by reference in its entirety.

FIELD OF THE INVENTION

The invention relates to polypeptides that find use in the prevention or treatment of Coronaviridae viral infection.

SEQUENCE LISTING

The instant application contains a Sequence Listing which has been submitted electronically in ASCII format and is hereby incorporated by reference in its entirety. Said ASCII copy, created on Jun. 29, 2020, is named 52895708201_SL.txt and is 43,351 bytes in size.

SUMMARY OF THE INVENTION

Disclosed herein, in certain embodiments, are polypeptide vaccines, comprising a polypeptide comprising an amino acid sequence selected from the group consisting of SEQ ID NOs: 1 to 17, and a pharmaceutically-acceptable adjuvant, diluent, carrier, preservative, excipient, buffer, stabilizer, or combination thereof. In some embodiments, the polypeptide vaccines comprise two or more polypeptides, each polypeptide comprising a different amino acid sequence selected from the group consisting of SEQ ID NOs: 1 to 17. In some embodiments, the polypeptide vaccines comprise at least one polypeptide from at least two of the following groups: (a) SEQ ID NOs: 1 to 11; (b) SEQ ID NOs: 12 to 15; (c) SEQ ID NO: 16; and (d) SEQ ID NO: 17. In some embodiments, the polypeptide vaccines comprise at least two polypeptides, wherein each polypeptide comprises a different one of the amino acid sequences of SEQ ID NOs: 2, 5, 7, 9, 12, 13, 14, 15, 16, and 17. In some embodiments, the polypeptide vaccines comprise at least four polypeptides, wherein each polypeptide comprises a different one of the amino acid sequences of SEQ ID NOs: 2, 5, 7, 9, 12, 13, 14, 15, 16, and 17. In some embodiments, the polypeptide vaccines comprise at least six polypeptides, wherein each polypeptide comprises a different one of the amino acid sequences of SEQ ID NOs: 2, 5, 7, 9, 12, 13, 14, 15, 16, and 17. In some embodiments, the polypeptide vaccines comprise at least eight polypeptides, wherein each polypeptide comprises a different one of the amino acid sequences of SEQ ID NOs: 2, 5, 7, 9, 12, 13, 14, 15, 16, and 17. In some embodiments, the polypeptide vaccines comprise at least ten polypeptides, wherein each polypeptide comprises a different one of the amino acid sequences of SEQ ID NOs: 2, 5, 7, 9, 12, 13, 14, 15, 16, and 17. In some embodiments, the one or more of the polypeptides comprises a fragment of a Coronaviridae protein that is a CD8+ T cell epitope that is restricted to at least two HLA class I alleles of the individual. In some embodiments, the one or more of the polypeptides comprises a fragment of a Coronaviridae protein that is a CD4+ T cell epitope restricted to at least two HLA class II alleles of the individual. In some embodiments, the one or more of the polypeptides comprises a linear B cell epitope.

Disclosed herein, in certain embodiments, are methods treating or preventing a Coronaviridae infection in an individual in need thereof, comprising administering to the individual a polypeptide vaccine disclosed herein. In some embodiments, the Coronaviridae infection is a SARS-CoV-2 infection.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DESCRIPTION OF THE SEQUENCES

Figure 1:
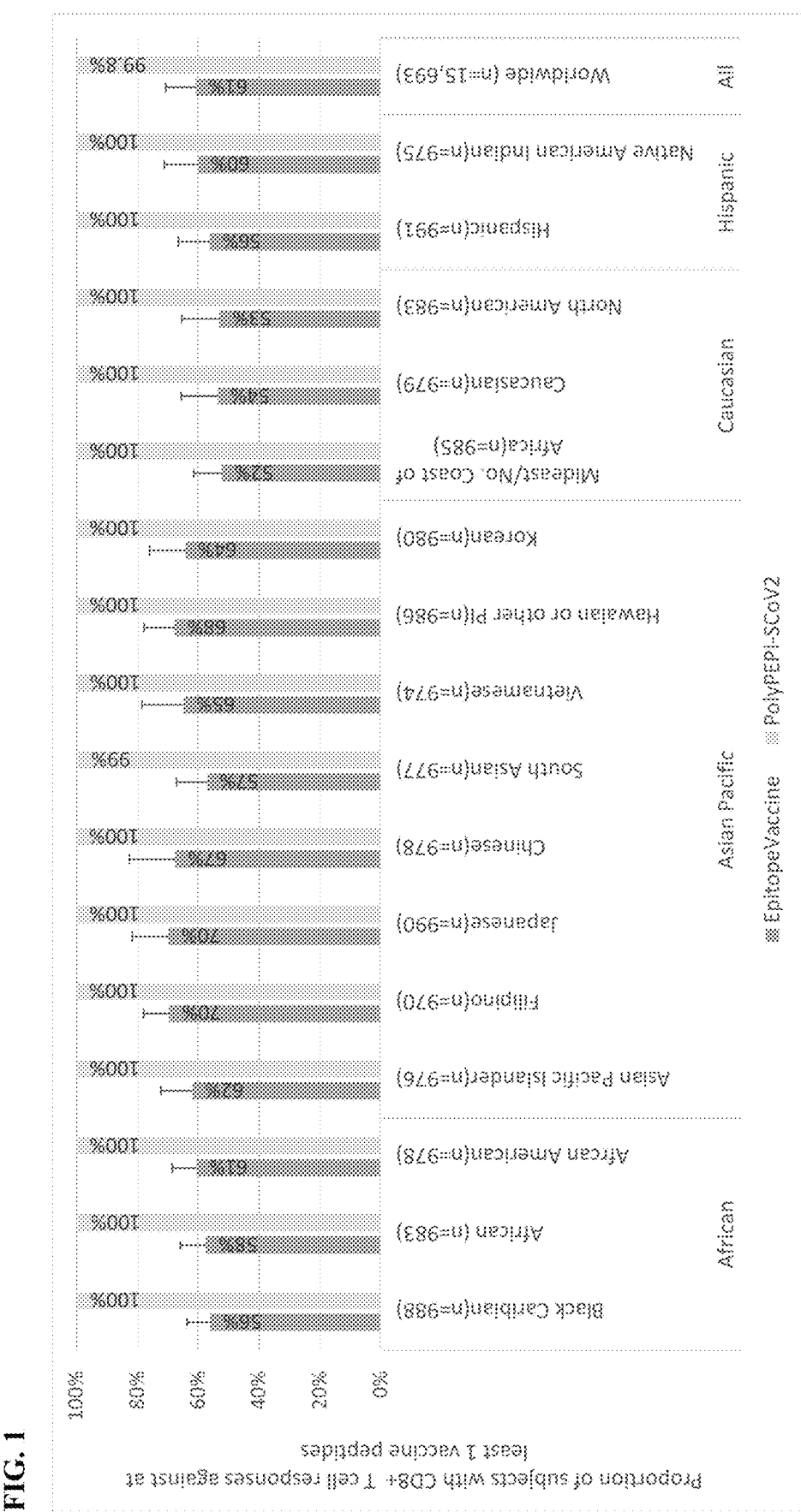
FIG. 1. Comparison of predicted vaccine induced immune response rates (CD8) for randomly selected Epitope Vaccine proposed by SF Ahmed et al. and 10 peptides of PolyPEPI-SCoV2 vaccine in ~16,000 individuals of 16 ethnicities.

SEQ ID NOs: 1 to 17 set forth 30 mer T cell epitopes described in Table 2A.

DETAILED DESCRIPTION OF THE INVENTION

SARS-CoV-2 is similar to SARS-CoV, for which previous research data exist on protective immune responses. Both the humoral and cell-mediated immune responses appear to play a protective role against SARS-CoV. Antibody responses generated against the spike (S) and nucleocapsid (N) protein of SARS-CoV are particularly prevalent in SARS-CoV-infected patients. While being effective, the antibody response is short-lived in convalescent SARS-CoV patients. In contrast, T cell responses provide long-term memory post-infection in recovered patients.

One of the challenges of producing an effective vaccine is that there is tremendous variability in the way the immune systems of different human individuals interact with the different antigens expressed by an infecting virus. Previously, it has been shown that the immune response of an individual is predicted by the ability of single antigen T cell epitopes to be recognized by multiple HLA alleles of the individual. T cell epitopes that are restricted to multiple HLA alleles of an individual act as genetic biomarkers that predict peptide-specific T cell responses of individual patients. These genetic biomarkers are referred to as "personal epitopes" or "PEPIs". Multi-HLA allele-binding PEPIs induce T cell responses at a significantly higher rate than T cell epitopes that are restricted to a single HLA allele of a vaccinated individual. The identification of T cell epitopes in the polypeptides of a vaccine composition that are multi-HLA allele-binding PEPIs for individuals in a model human population has been shown to predict the immune response rates reported in clinical trials (WO 2018/158456, WO 2018/158457 and WO 2018/158455).

A second challenge in the development of an effective vaccine is the continuing evolution of the virus through mutation and the potential for infecting virus heterogeneity.

A third challenge is the need to quickly develop, safety test, and verify efficacy of a vaccine for the new emergent SARS-CoV-2 coronavirus virus, and subsequently manufacture the vaccine on a very large scale, to meet immediate population demands. Conventional vaccine development is a complex and challenging process. Peptide vaccines provide several advantages in comparison to conventional vaccines made of dead or attenuated pathogens, inactivated toxins, and recombinant subunits. Short polypeptides can be synthesized rapidly and peptide vaccine production is relatively inexpensive. Additionally, peptide vaccines avoid the inclusion of unnecessary components possessing high reactogenicity to the host, such as lipopolysaccharides, lipids, and toxins.

Peptide vaccine development strategy typically targets the selection of a combination of HLA allele-restricted epitopes that seek to maximize population coverage globally. According to this approach, multiple peptides are selected having different HLA binding specificities to afford increased coverage of the patient population targeted by peptide (epitope)-based vaccines, taking also in consideration that different HLA types are expressed at dramatically different frequencies in different ethnicities.

One recent approach proposed to screen a set of T cell epitopes estimated to provide broad coverage of global population as well as in China against SARS-CoV-2. This approach used HLA-restricted SARS-CoV-derived epitopes and the publicly available IEDB Population Coverage Tool (tools.iedb.org/population) to guide experimental efforts towards the development of vaccines against SARS-CoV-2. This approach attempts to take in consideration HLA polymorphism and frequency in different ethnic populations. In practice, however, most often HLA-restricted epitopes do not induce an immune response in HLA-matched individuals, and clinical trials result in lower immune response rates than expected. In addition, peptides recognized by CD8 T cells have been shown to be both selective and extremely sensitive; one amino acid change can alter the specific epitope into a non-immunogenic peptide.

Other approaches include the whole sequence of S protein in mRNA or pDNA vectors.

Accordingly, there is an immediate need for a vaccine that is effective in a high proportion of the global human population, robust to viral antigen mutation, and could proceed rapidly through the necessary steps for clinical validation and manufacture.

Disclosed herein, in certain embodiments, are polypeptide vaccines against SARS-CoV-2 that addresses the dual challenges of heterogeneity in the immune responses of different individuals, and potential heterogeneity in the infecting virus. In some embodiments, the peptides disclosed herein merge personal epitope design with the further selection of B cell epitope sequences resulting in overlapping, multi-HLA binding epitopes within an individual aiming to induce CD4+, CD8+ and antibody-producing B-cell responses. In some embodiments, the peptide vaccines comprise a selection of 30mer polypeptide fragments of the conserved regions of SARS-CoV-2 viral antigens that comprise (i) maximum CD8+ personal epitopes (PEPIs) in a model population of human individuals having HLA genotypes that are representative of the global population; (ii) maximum CD4+ personal epitopes (PEPIs) in the global population; and (iii) linear B cell epitopes. In some embodiments, the vaccines disclosed herein induce cytotoxic T cell, helper T cell and B cell responses in a surprisingly high proportion of individuals in the human population.

Disclosed herein, in certain embodiments, are polypeptide vaccines comprising at least one polypeptide comprising an amino acid sequence selected from SEQ ID NOs: 1 to 17, and a pharmaceutically-acceptable excipient. In some embodiments, the polypeptide vaccine comprises at least two different polypeptides comprising an amino acid sequence selected from SEQ ID NOs: 1 to 17.

Disclosed herein, in certain embodiments, are polypeptide vaccines comprising at least one polypeptide comprising a fragment of a Coronaviridae, Betacoronavirus or SARS-CoV-2 protein. In some embodiments, the polypeptide vaccine comprises at least one amino acid sequence selected from SEQ ID NOs: 1 to 17. In some embodiments, the polypeptide vaccine comprises at least one sequence from at least two of the following groups: (a) SEQ ID NOs: 1 to 11 (fragments of SARS-CoV-2 surface protein); (b) SEQ ID NOs: 12 to 15 (fragments of SARS-CoV-2 nucleocapsid protein); (c) SEQ ID NO: 16 (fragment of SARS-CoV-2 membrane protein); and (d) SEQ ID NO: 17 (fragment of SARS-CoV-2 envelope protein). In some embodiments, the polypeptide vaccine comprises at least 3, 4, 5, 6, 7, 8, 9, 10, 11, 12, 13, 14, 15, 16 or 17 different polypeptides, each comprising a different amino acid sequence selected from SEQ ID NOs: 1 to 17. In some embodiments, the polypeptide vaccine comprises ten polypeptides comprising an amino acid sequence of SEQ ID NOs: 2, 5, 7, 9, 12, 13, 14, 15, 16, and 17.

Disclosed herein, in certain embodiments, are methods of treating or preventing a SARS-CoV-2 infection in an individual in need thereof, comprising administering to the individual a polypeptide vaccine comprising at least one polypeptide comprising an amino acid sequence selected from SEQ ID NOs: 1 to 17, and a pharmaceutically-acceptable excipient. In some embodiments, the polypeptide vaccine comprises at least two different polypeptides comprising an amino acid sequence selected from SEQ ID NOs: 1 to 17. In some embodiments, at least one polypeptide comprises a CD8+ T cell epitope that is restricted to at least two, or in some cases three or at least three, HLA class I alleles of the individual. In some embodiments, at least one polypeptide comprises a CD4+ T cell epitope that is restricted to at least two, or in some cases at least three, or in some cases four or at least four, HLA class II alleles of the individual. In some embodiments, at least one polypeptide comprises a linear B cell epitope. In some cases, the method further comprises the step of determining the HLA class I and/or class II genotype of the individual.

Disclosed herein, in certain embodiments, are methods of treating or preventing a Coronaviridae, Betacoronavirus or SARS-CoV-2 infection in an individual in need thereof, comprising administering to the individual a polypeptide vaccine comprising at least one polypeptide comprising a fragment of a Coronaviridae, Betacoronavirus or SARS-CoV-2 protein. In some embodiments, at least one polypeptide comprises a CD8+ T cell epitope that is restricted to at least two, or in some cases three or at least three, HLA class I alleles of the individual. In some embodiments, at least one polypeptide comprises a CD4+ T cell epitope that is restricted to at least two, or in some cases at least three, or in some cases four or at least four, HLA class II alleles of the individual. In some embodiments, at least one polypeptide comprises a linear B cell epitope. In some embodiments, the polypeptide vaccine comprises at least one amino acid sequence selected from SEQ ID NOs: 1 to 17. In some embodiments, the polypeptide vaccine comprises at least one sequence from at least two of the following groups: (a) SEQ ID NOs: 1 to 11 (fragments of SARS-CoV-2 surface protein); (b) SEQ ID NOs: 12 to 15 (fragments of SARS-CoV-2 nucleocapsid protein); (c) SEQ ID NO: 16 (fragment of SARS-CoV-2 membrane protein); and (d) SEQ ID NO: 17 (fragment of SARS-CoV-2 envelope protein). In some embodiments, the polypeptide vaccine comprises at least 3, 4, 5, 6, 7, 8, 9, 10, 11, 12, 13, 14, 15, 16 or 17 different polypeptides, each comprising a different amino acid sequence selected from SEQ ID NOs: 1 to 17. In some embodiments, the polypeptide vaccine comprises ten polypeptides comprising an amino acid sequence of SEQ ID NOs: 2, 5, 7, 9, 12, 13, 14, 15, 16, and 17. In some cases, the method further comprises the step of determining the HLA class I and/or class II genotype of the individual.

The disclosure will now be described in more detail, by way of example and not limitation, and by reference to the accompanying drawings. Many equivalent modifications and variations will be apparent, to those skilled in the art when given this disclosure. Accordingly, the exemplary embodiments of the disclosure set forth are considered to be illustrative and not limiting. Various changes to the described embodiments may be made without departing from the scope of the disclosure. All documents cited herein, whether supra or infra, are expressly incorporated by reference in their entirety.

The present disclosure includes the combination of the aspects and preferred features described except where such a combination is clearly impermissible or is stated to be expressly avoided. As used in this specification and the appended claims, the singular forms "a", "an", and "the" include plural referents unless the content clearly dictates otherwise. Thus, for example, reference to "a peptide" includes two or more such peptides.

Section headings are used herein for convenience only and are not to be construed as limiting in any way.

HLA Genotypes

HLAs are encoded by the most polymorphic genes of the human genome. Each person has a maternal and a paternal allele for the three HLA class I molecules (HLA-A*, HLA-B*, HLA-C*) and four HLA class II molecules (HLA-DP*, HLA-DQ*, HLA-DRB1*, HLA-DRB3*/4*/5*). Practically, each person expresses a different combination of 6 HLA class I and 8 HLA class II molecules that present different epitopes from the same protein antigen.

The nomenclature used to designate the amino acid sequence of the HLA molecule is as follows: gene name*allele:protein number, which, for instance, can look like: HLA-A*02:25. In this example, "02" refers to the allele. In most instances, alleles are defined by serotypes—meaning that the proteins of a given allele will not react with each other in serological assays. Protein numbers ("25" in the example above) are assigned consecutively as the protein is discovered. A new protein number is assigned for any protein with a different amino acid sequence (e.g. even a one amino acid change in sequence is considered a different protein number). Further information on the nucleic acid sequence of a given locus may be appended to the HLA nomenclature.

The HLA class I genotype or HLA class II genotype of an individual may refer to the actual amino acid sequence of each class I or class II HLA of an individual, or may refer to the nomenclature, as described above, that designates, minimally, the allele and protein number of each HLA gene. An HLA genotype may be determined using any suitable method. For example, the sequence may be determined via sequencing the HLA gene loci using methods and protocols known in the art. Alternatively, the HLA set of an individual may be stored in a database and accessed using methods known in the art.

Some individuals may have two HLA alleles that encode the same HLA molecule (for example, two copies for HLA-A*02:25 in case of homozygosity). The HLA molecules encoded by these alleles bind all of the same T cell epitopes. For the purposes of this disclosure "binding to at least two HLA molecules of the individual" as used herein includes binding to the HLA molecules encoded by two identical HLA alleles in a single individual. In other words, "binding to at least two HLA molecules of the individual" and the like could otherwise be expressed as "binding to the HLA molecules encoded by at least two HLA alleles of the individual".

Polypeptides

Disclosed herein, in certain embodiments, are polypeptide vaccines that are derived from SARS-CoV-2 antigens and that are immunogenic for a high proportion of the human population.

As used herein, the terms "peptide" and "polypeptide" refer to chains of amino acids comprising between 2, or 3, or 4, or 5, or 6, or 7, or 8, or 9, or 10, or 11, or 12, or 13, or 14, or 15 and 10, or 11, or 12, or 13, or 14, or 15, or 20, or 25, or 30, or 35, or 40, or 45, or 50 or 55 or 60 amino acids. The terms "peptide" and "polypeptide" are used interchangeably. In some embodiments, the polypeptides disclosed herein comprise 30 amino acids.

As used herein, the term "epitope" or "T cell epitope" refers to a sequence of contiguous amino acids contained within a protein antigen that possess a binding affinity for (is capable of binding to) one or more HLAs. An epitope is HLA- and antigen-specific (HLA-epitope pairs, predicted with known methods), but not individual specific. An epitope, a T cell epitope, a polypeptide, a fragment of a polypeptide or a composition comprising a polypeptide or a fragment thereof is "immunogenic" for a specific human individual if it is capable of inducing a T cell response (a cytotoxic T cell response or a helper T cell response) in that individual. In some cases, the helper T cell response is a Th1-type helper T cell response. The terms "T cell response" and "immune response" are used herein interchangeably, and refer to the activation of T cells and/or the induction of one or more effector functions following recognition of one or more HLA-epitope binding pairs. In some cases, an "immune response" includes an antibody response, because HLA class II molecules stimulate helper responses that are involved in inducing both long lasting CTL responses and antibody responses. Effector functions include cytotoxicity, cytokine production and proliferation. According to the present disclosure, an epitope, a T cell epitope, or a fragment of a polypeptide is immunogenic for a specific individual if it is capable of binding to at least two, or in some cases at least three, class I or at least two, or in some cases at least three or at least four class II HLAs of the individual.

A "personal epitope" (or "PEPI") is a fragment of a polypeptide consisting of a sequence of contiguous amino acids of the polypeptide that is a T cell epitope capable of binding to one or more HLA class I molecules of a specific human individual. In other cases, a "PEPI" is a fragment of a polypeptide consisting of a sequence of contiguous amino acids of the polypeptide that is a T cell epitope capable of binding to one or more HLA class II molecules of a specific human individual. In other words, a "PEPI" is a T cell epitope that is recognized by the HLA set of a specific individual, and is consequently specific to the individual in addition to the HLA and the antigen. In contrast to an "epitope", which is specific only to HLA and the antigen, PEPIs are specific to an individual because different individuals have different HLA molecules which each bind to different T cell epitopes.

"PEPI1" as used herein refers to a peptide, or a fragment of a polypeptide, that can bind to one HLA class I molecule (or, in specific contexts, HLA class II molecule) of an individual. "PEPI1+" refers to a peptide, or a fragment of a polypeptide, that can bind to one or more HLA class I molecule of an individual. "PEPI2" refers to a peptide, or a fragment of a polypeptide, that can bind to two HLA class I (or II) molecules of an individual. "PEPI2+" refers to a peptide, or a fragment of a polypeptide, that can bind to two or more HLA class I (or II) molecules of an individual. "PEPI3" refers to a peptide, or a fragment of a polypeptide, that can bind to three HLA class I (or II) molecules of an individual. "PEPI3+" refers to a peptide, or a fragment of a polypeptide, that can bind to three or more HLA class I (or II) molecules of an individual. "PEPI4" refers to a peptide, or a fragment of a polypeptide, that can bind to three HLA class I (or II) molecules of an individual. "PEPI4+" refers to a peptide, or a fragment of a polypeptide, that can bind to three or more HLA class I (or II) molecules of an individual.

Generally speaking, epitopes presented by HLA class I molecules are about nine amino acids long and epitopes presented by HLA class II molecules are about fifteen amino acids long. For the purposes of this disclosure, however, an epitope may be more or less than nine (for HLA Class I) or fifteen (for HLA Class II) amino acids long, as long as the epitope is capable of binding HLA. For example, an epitope that is capable of binding to class I HLA may be between 7, or 8 or 9 and 9 or 10 or 11 amino acids long. An epitope that is capable of binding to a class II HLA may be between 13, or 14 or 15 and 15 or 16 or 17 amino acids long.

A given HLA of an individual will only present to T cells a limited number of different peptides produced by the processing of protein antigens in an antigen presenting cell (APC). As used herein, "display" or "present", when used in relation to HLA, references the binding between a peptide (epitope) and an HLA. In this regard, to "display" or "present" a peptide is synonymous with "binding" a peptide.

Any suitable method is used to determine the epitopes that will bind to a known HLA. For example, biochemical analysis may be used. It is also possible to use lists of epitopes known to be bound by a given HLA. It is also possible to use predictive or modelling software to determine which epitopes may be bound by a given HLA. Examples are provided in Table 1. In some cases, a T cell epitope is capable of binding to a given HLA if it has an IC50 or predicted IC50 of less than 5000 nM, less than 2000 nM, less than 1000 nM, or less than 500 nM.

TABLE 1

Example software for determining epitope-HLA binding

| EPITOPE PREDICTION TOOLS | WEB ADDRESS |
|---|---|
| BIMAS, NIH | bimas.cit.nih.gov/molbio/hla_bind/ |
| PPAPROC, Tubingen Univ. | |
| MHCPred, Edward Jenner Inst. of Vaccine Res. | |
| EpiJen, Edward Jenner Inst. of Vaccine Res. | ddg-pharmfac.net/epijen/EpiJen/EpiJen.htm |
| NetMHC, Center for Biological Sequence Analysis | cbs.dtu.dk/services/NetMHC/ |
| SVMHC Tubingen Univ. | abi.inf.uni-tuebingen.de/Services/SVMHC/ |
| SYFPEITHI, Biomedical Informatics, Heidelberg | syfpeithi.de/bin/MHCServer.dll/EpitopePrediction.htm |
| ETK EPITOOLKIT, Tubingen Univ. | etk.informatik.uni-tuebingen.de/epipred/ |
| PREDEP, Hebrew Univ. Jerusalem | margalit.huji.ac.il/Teppred/mhc-bind/index.html |
| RANKPEP, MIF Bioinformatics | bio.dfci.harvard.edu/RANKPEP/ |
| IEDB, Immune Epitope Database | tools.immuneepitope.org/main/html/tcell_tools.html |
| MHCBN, Institute of Microbial Technology, Chandigarh, INDIA | imtech.res.in/raghava/mhcbn/ |
| SYFPEITHI, Biomedical Informatics, Heidelberg | syfpeithi.de/ |
| AntiJen, Edward Jenner Inst. of Vaccine Res. | ddg-pharmfac.net/antijen/AntiJen/antijenhomepage.htm |
| EPIMHC database of MHC ligands, MIF Bioinformatics | immunax.dfci.harvard.edu/epimhc/ |
| IEDB, Immune Epitope Database | iedb.org/ |

In some embodiments, the peptides disclosed herein comprise or consist of one or more fragments of one or more Coronaviridae, a Betacoronavirus or SARS-CoV-2 antigens selected from surface glycoprotein, alias Spike, nucleocapsid phosphoprotein, envelope protein and membrane glycoprotein. Reference sequences are provided herein.

In some embodiments, the amino acid sequence is flanked at the N and/or C terminus by additional amino acids that are not part of the sequence of the Coronaviridae, Betacoronavirus or SARS-CoV-2 antigen, in other words that are not the same sequence of consecutive amino acids found adjacent to the selected fragments in the target polypeptide antigen. In some embodiments, the sequence is flanked by up to 30, 29, 28, 27, 26, 25, 24, 23, 22, 21, 20, 19, 18, 17, 16, 15, 14, 13, 12, 11, 10, 9, 8, 7, 6, 5, 4, 3, 2 or 1 additional amino acids at the N and/or C terminus.

It has been shown that the presence in a cancer vaccine of at least two polypeptide fragments (epitopes) that can bind to at least three HLA class I of an individual (≥2 PEPI3+) is predictive for a clinical response. In other words, if ≥2 PEPI3+ can be identified within the active ingredient polypeptide(s) of a vaccine, then an individual is a likely clinical responder.

Without wishing to be bound by theory, it is believed that one reason for the increased likelihood of deriving clinical benefit from a vaccine/immunotherapy comprising at least two multiple-HLA binding PEPIs, is that diseased cell populations, such as cancer or tumor cells or cells infected by viruses or pathogens such as HIV, are often heterogeneous both within and between affected individuals. In addition, the likelihood of developing resistance is decreased when more multiple HLA-binding PEPIs are included or targeted by a vaccine because a patient is less likely to develop resistance to the composition through mutation of the target PEPI(s).

Likewise, in the context of a vaccine for a viral infection, where the viral infection may be heterologous, it is advantageous to administer to an individual vaccine peptide(s) that are predicted to comprise multiple individual-specific multi-HLA allele-binding PEPIs (for treatment of an individual having a known HLA genotype) or multiple population bestEPIs, i.e. amino acid sequences that are or comprise multi-HLA allele-binding PEPIs in a high proportion of the target population. Including more bestEPI sequences also increases the total proportion of human individuals that will respond to treatment. Accordingly, in some embodiments, the polypeptide vaccine comprises at least 2, 3, 4, 5, 6, 7, 8, 9, 10, 11, 12, 13, 14, 15, 16 or 17 polypeptides, each comprising a different amino acid sequence selected from SEQ ID NOs: 1 to 17. In some embodiments, the combination of polypeptides excludes one or more of the following combinations: SEQ ID NOs: 1 and 2; SEQ ID NOs: 3 and 4; SEQ ID NOs: 7 and 8; and/or SEQ ID NOs: 9 and 10; and/or excludes one or more of the following combinations: SEQ ID NOs: 2 and 3; and/or SEQ ID NOs: 13 and 14.

In some embodiments, the polypeptide vaccine comprises fragments of the same or different viral antigens. Different viral structural proteins may tend to mutate at different rates. Hence, in some embodiments, each polypeptide comprises an amino acid sequence selected from SEQ ID NOs: 1 to 17 that is a fragment of a different Coronaviridae, a Betacoronavirus or SARS-CoV-2 protein. In some embodiments, the polypeptide vaccine includes at least one sequence from at least two, three or all four of the following groups: (a) SEQ ID NOs: 1 to 11 (fragments of SARS-CoV-2 surface protein), optionally excluding the combination of SEQ ID NOs: 1 and 2, SEQ ID NOs: 2 and 3, SEQ ID NOs: 3 and 4, SEQ ID NOs: 7 and 8, and/or SEQ ID NOs: 9 and 10; (b) SEQ ID NOs: 12 to 15 (fragments of SARS-CoV-2 nucleocapsid protein), optionally excluding the combination of SEQ ID NOs: 13 and 14; (c) SEQ ID NO: 16 (fragment of SARS-CoV-2 membrane protein); and (d) SEQ ID NO: 17 (fragment of SARS-CoV-2 envelope protein). In some embodiments, the combination of polypeptides comprises or consists of ten polypeptides comprising or consisting of the amino acid sequences of SEQ ID NOs: 2, 5, 7, 9, 12, 13, 14, 15, 16, and 17.

Selection of Polypeptides and Patients

In some embodiments, the peptides described herein induce T cell responses or provide vaccination in an individual in need therefore. In some embodiments, the peptides treat or prevent a Coronaviridae infection, a Betacoronavirus infection or SARS-CoV-2 infection (COVID-19) in an individual. More than one peptide will typically be selected for treatment of an individual. In some cases, the peptide(s) used for treatment may be selected based on (i) the disease or condition to be treated in the individual; (ii) the HLA genotype of the individual; and/or (iii) the genetic background of the individual (e.g. nationality or ethnic group).

Polypeptide antigens, and particularly short peptides derived from polypeptide antigens, that are commonly used in vaccination and immunotherapy, induce immune responses in only a fraction of human individuals. The peptides of the present disclosure are specifically selected to induce immune responses in a high proportion of the global population. However, but they may not be effective in all individuals due to HLA genotype heterogeneity.

The present inventors have discovered that multiple HLA expressed by an individual generally need to present the same peptide in order to trigger a T cell response. Therefore, the fragments of a polypeptide antigen (epitopes) that are predicted to be immunogenic for a specific individual (PEPIs) are those that can bind to multiple class I (activate cytotoxic T cells) or class II (activate helper T cells) HLAs expressed by that individual. In general, a cytotoxic T-cell response in an individual to a specific vaccine peptide is best predicted by the presence in the vaccine peptide of ≥1 PEPI3+(epitope that binds to three or more class I HLA alleles of the individual). A helper T cell response is generally best predicted by ≥1 PEPI3+ or ≥1 PEPI4+(epitope that binds to three or more or four or more class II HLA alleles of the individual).

Accordingly, disclosed herein, in certain embodiments, are methods of predicting that a human individual will have a T cell response (cytotoxic and/or helper) to administration of a panel of polypeptides or a pharmaceutical composition as described herein. In some embodiments, the methods comprise (A) (i) determining that the panel of polypeptides or the active ingredient polypeptide(s) of the pharmaceutical composition comprise a T cell epitope that is restricted to at least three HLA class I molecules of the individual; and (ii) predicting that the individual will have a cytotoxic (CD8+) T cell response to administration of the panel of polypeptides or the pharmaceutical composition; and/or (B) (i) determining that the panel of polypeptides or the active ingredient polypeptide(s) of the pharmaceutical composition comprise a T cell epitope that is restricted to at least three, or in some cases at least four HLA class II molecules of the individual; and (ii) predicting that the individual will have a helper (CD4+) T cell response to administration of the panel of polypeptides or the pharmaceutical composition.

Further disclosed herein, in certain embodiments, are methods of determining a probability that a specific human individual will have a T cell response (cytotoxic/CD8+ or helper/CD4+) to administration of a panel of polypeptides or pharmaceutical composition described herein, wherein the method comprises identifying T cell epitopes in the polypeptides or active ingredient polypeptides that are restricted to at least three HLA class I or at least three or at least four HLA class II of the individual, and wherein (A) (a) a higher number T cell epitopes that are restricted to at least three HLA class I of the individual; and/or (b) a higher number of T cell epitopes that are both (I) restricted to at least three HLA class I of the individual; and (II) fragments of different SARS-CoV-2 structural proteins, corresponds to a higher probability of a cytotoxic/CD8+ T cell response in the individual; and/or (B) (a) a higher number T cell epitopes that are restricted to at least three or at least four HLA class II of the individual; and/or (b) a higher number of T cell epitopes that are both (I) restricted to at least three or at least four HLA class II of the individual; and (II) fragments of different SARS-CoV-2 structural proteins, corresponds to a higher probability of a helper/CD4+ T cell response in the individual.

In some embodiments, the individual is predicted to have a cytotoxic T cell response, or higher than a predetermined threshold probability of having a cytotoxic T cell response to administration of the panel of peptides or the pharmaceutical composition, and the method further comprises selecting or recommending administration of the pharmaceutical composition as a method of treating the individual, and optionally further comprises treating the individual by administering the panel of polypeptides or the pharmaceutical composition to the individual.

Additionally disclosed herein, in certain embodiments, are methods of treatment as described herein, wherein the individual receiving treatment has been predicted to have a cytotoxic or helper T cell response to administration of the panel of polypeptides or the pharmaceutical composition using a method described herein, or higher than a predetermined threshold probability of having a cytotoxic T or helper cell response to administration of the panel of polypeptides or the pharmaceutical composition using a method described herein.

The presence in a vaccine or immunotherapy composition of at least two T cell epitopes that (i) correspond to fragments of one or more target polypeptide antigens, and (ii) can bind to at least three HLA class I alleles of an individual is predictive for a clinical response. A "clinical response" or "clinical benefit" as used herein may be the prevention or a delay in the onset of a disease or condition, the amelioration of one or more symptoms, the induction or prolonging of remission, or the delay of a relapse or recurrence or deterioration, or any other improvement or stabilization in the disease status of an individual. A clinical response may be also the prevention of infections caused by different mutated variants of Coronavidiae viruses.

Accordingly, disclosed herein, in certain embodiments, are methods of predicting that a specific human individual will have a clinical response to a method of treatment as described herein or to administration of a panel of peptides or pharmaceutical composition as described herein, or of determining a probability of a clinical response. The method is similar to that described herein for predicting a T cell response, but a clinical response is predicted by determining that the panel of polypeptides or the active ingredient polypeptide(s) of the pharmaceutical composition comprise two different T cell epitopes that are each restricted to at least three HLA class I molecules of the individual.

Pharmaceutical Compositions, Methods of Treatment and Modes of Administration

Disclosed herein, in certain embodiments, are pharmaceutical compositions or vaccines comprising one or more of the peptides, polynucleic acids or vectors described herein. Such pharmaceutical compositions or vaccines are used in methods of inducing an immune response, treating, vaccinating or providing immunotherapy to an individual. The methods of treatment described herein comprise administering the pharmaceutical composition to the individual.

The pharmaceutical compositions or vaccines described herein comprise, in addition to one or more peptides, nucleic acids or vectors, a pharmaceutically acceptable excipient, carrier, diluent, buffer, stabilizer, preservative, adjuvant or other materials well known to those skilled in the art. Such materials are preferably non-toxic and preferably do not interfere with the pharmaceutical activity of the active ingredient(s). The pharmaceutical carrier or diluent may be, for example, water containing solutions. The precise nature of the carrier or other material may depend on the route of administration, e.g. oral, intravenous, cutaneous or subcutaneous, nasal, intramuscular, intradermal, and intraperitoneal routes.

In some embodiments, the pharmaceutical compositions of the disclosure comprise one or more "pharmaceutically acceptable carriers". These are typically large, slowly metabolized macromolecules such as proteins, saccharides, polylactic acids, polyglycolic acids, polymeric amino acids, amino acid copolymers, sucrose (Paoletti, 2001, Vaccine, 19:2118-2126), trehalose (WO 00/56365), lactose and lipid aggregates (such as oil droplets or liposomes). Such carriers are well known to those of ordinary skill in the art. In some embodiments, the pharmaceutical compositions contain diluents, such as water, saline, glycerol, etc. Additionally, auxiliary substances, such as wetting or emulsifying agents, pH buffering substances, and the like, may be present. Sterile pyrogen-free, phosphate buffered physiologic saline is a typical carrier (Gennaro, 2000, Remington: The Science and Practice of Pharmacy, 20th edition, ISBN:0683306472).

In some embodiments, the pharmaceutical compositions of the disclosure are lyophilized or in aqueous form, i.e. solutions or suspensions. Liquid formulations of this type allow the compositions to be administered direct from their packaged form, without the need for reconstitution in an aqueous medium, and are thus ideal for injection. In some embodiments, the pharmaceutical compositions are presented in vials, or they may be presented in ready filled syringes. The syringes may be supplied with or without needles. A syringe will include a single dose, whereas a vial may include a single dose or multiple doses.

Liquid formulations of the disclosure are also suitable for reconstituting other medicaments from a lyophilized form. Where a pharmaceutical composition is to be used for such extemporaneous reconstitution, the disclosure provides a kit, which may comprise two vials, or may comprise one ready-filled syringe and one vial, with the contents of the syringe being used to reconstitute the contents of the vial prior to injection.

In some embodiments, the pharmaceutical compositions of the disclosure include an antimicrobial, particularly when packaged in a multiple dose format. Antimicrobials may be used, such as 2-phenoxyethanol or parabens (methyl, ethyl, propyl parabens). Any preservative is preferably present at low levels. Preservative may be added exogenously and/or may be a component of the bulk antigens which are mixed to form the composition (e.g. present as a preservative in pertussis antigens).

In some embodiments, the pharmaceutical compositions of the disclosure comprise detergent e.g. Tween (polysorbate), DMSO (dimethyl sulfoxide), DMF (dimethylformamide). Detergents are generally present at low levels, e.g. <0.01%, but may also be used at higher levels, e.g. 0.01-50%.

In some embodiments, the pharmaceutical compositions of the disclosure include sodium salts (e.g. sodium chloride) and free phosphate ions in solution (e.g. by the use of a phosphate buffer).

In some embodiments, the pharmaceutical compositions are encapsulated in a suitable vehicle either to deliver the peptides into antigen presenting cells or to increase the stability. As will be appreciated by a skilled artisan, a variety of vehicles are suitable for delivering a pharmaceutical composition of the disclosure. Non-limiting examples of suitable structured fluid delivery systems may include nanoparticles, liposomes, microemulsions, micelles, dendrimers and other phospholipid-containing systems. Methods of incorporating pharmaceutical compositions into delivery vehicles are known in the art.

In order to increase the immunogenicity of the composition, in some embodiments, the pharmacological compositions comprise one or more adjuvants and/or cytokines.

Suitable adjuvants include an aluminum salt such as aluminum hydroxide or aluminum phosphate, but may also be a salt of calcium, iron or zinc, or may be an insoluble suspension of acylated tyrosine, or acylated sugars, or may be cationically or anionically derivatized saccharides, polyphosphazenes, biodegradable microspheres, monophosphoryl lipid A (MPL), lipid A derivatives (e.g. of reduced toxicity), 3-O-deacylated MPL [3D-MPL], quil A, Saponin, QS21, Freund's Incomplete Adjuvant (Difco Laboratories, Detroit, Mich.), Merck Adjuvant 65 (Merck and Company, Inc., Rahway, N.J.), AS-2 (Smith-Kline Beecham, Philadelphia, Pa.), CpG oligonucleotides, bioadhesives and mucoadhesives, microparticles, liposomes, polyoxyethylene ether formulations, polyoxyethylene ester formulations, muramyl peptides or imidazoquinolone compounds (e.g. imiquamod and its homologues). Human immunomodulators suitable for use as adjuvants in the disclosure include cytokines such as interleukins (e.g. IL-1, IL-2, IL-4, IL-5, IL-6, IL-7, IL-12, etc), macrophage colony stimulating factor (M-CSF), tumor necrosis factor (TNF), granulocyte, macrophage colony stimulating factor (GM-CSF) may also be used as adjuvants.

In some embodiments, the compositions comprise an adjuvant selected from the group consisting of Montanide ISA-51 (Seppic, Inc., Fairfield, N.J., United States of America), QS-21 (Aquila Biopharmaceuticals, Inc., Lexington, Mass., United States of America), GM-CSF, cyclophosamide, bacillus Calmette-Guerin (BCG), corynbacterium parvum, levamisole, azimezone, isoprinisone, dinitrochlorobenezene (DNCB), keyhole limpet hemocyanins (KLH), Freunds adjuvant (complete and incomplete), mineral gels, aluminum hydroxide (Alum), lysolecithin, pluronic polyols, polyanions, oil emulsions, dinitrophenol, diphtheria toxin (DT). In some embodiments, the adjuvant is Montanide adjuvant.

By way of example, the cytokine may be selected from the group consisting of a transforming growth factor (TGF) such as but not limited to TGF-α and TGF-β; insulin-like growth factor-I and/or insulin-like growth factor-II; erythropoietin (EPO); an osteoinductive factor; an interferon such as but not limited to interferon-α, -β, and -γ; a colony stimulating factor (CSF) such as but not limited to macrophage-CSF (M-CSF); granulocyte-macrophage-CSF (GM-CSF); and granulocyte-CSF (G-CSF). In some embodiments, the cytokine is selected from the group consisting of nerve growth factors such as NGF-β; platelet-growth factor; a transforming growth factor (TGF) such as but not limited to TGF-α. and TGF-β; insulin-like growth factor-I and insulin-like growth factor-II; erythropoietin (EPO); an osteoinductive factor; an interferon (IFN) such as but not limited to IFN-α, IFN-β, and IFN-γ; a colony stimulating factor (CSF) such as macrophage-CSF (M-CSF); granulocyte-macrophage-CSF (GM-CSF); and granulocyte-CSF (G-CSF); an interleukin (Il) such as but not limited to IL-1, IL-1.alpha., IL-2, IL-3, IL-4, IL-5, IL-6, IL-7, IL-8, IL-9, IL-10, IL-11, IL-12; IL-13, IL-14, IL-15, IL-16, IL-17, IL-18; LIF; kit-ligand or FLT-3; angiostatin; thrombospondin; endostatin; a tumor necrosis factor (TNF); and LT.

It is expected that an adjuvant or cytokine can be added in an amount of about 0.01 mg to about 10 mg per dose, preferably in an amount of about 0.2 mg to about 5 mg per dose. Alternatively, the adjuvant or cytokine may be at a concentration of about 0.01 to 50%, preferably at a concentration of about 2% to 30%.

In certain aspects, the pharmaceutical compositions of the disclosure are prepared by physically mixing the adjuvant and/or cytokine with peptides described herein under appropriate sterile conditions in accordance with known techniques to produce the final product.

In some embodiments, the compositions disclosed herein are prepared as a (ribo)nucleic acid vaccine. In some embodiments, the nucleic acid vaccine is a DNA vaccine. In some embodiments, DNA vaccines, or gene vaccines, comprise a plasmid with a promoter and appropriate transcription and translation control elements and a nucleic acid sequence encoding one or more polypeptides of the disclosure. In some embodiments, the plasmids also include sequences to enhance, for example, expression levels, intracellular targeting, or proteasomal processing. In some embodiments, DNA vaccines comprise a viral vector containing a nucleic acid sequence encoding one or more polypeptides of the disclosure. In additional aspects, the compositions disclosed herein comprise one or more nucleic acids encoding peptides determined to have immunoreactivity with a biological sample. For example, in some embodiments, the compositions comprise one or more nucleotide sequences encoding 1, 2, 3, 4, 5, 6, 7, 8, 9, 10, 11, 12, 13, 14, 15, 16, 17, 18, 19, 20, or more peptides comprising a fragment that is a T cell epitope capable of binding to at least three HLA class I molecules and/or at least three or four HLA class II molecules of a patient. In some embodiments, the DNA or gene vaccine also encodes immunomodulatory molecules to manipulate the resulting immune responses, such as enhancing the potency of the vaccine, stimulating the immune system or reducing immunosuppression. Strategies for enhancing the immunogenicity of DNA or gene vaccines include encoding of xenogeneic versions of antigens, fusion of antigens to molecules that activate T cells or trigger associative recognition, priming with DNA vectors followed by boosting with viral vector, and utilization of immunomodulatory molecules. In some embodiments, the DNA vaccine is introduced by a needle, a gene gun, an aerosol injector, with patches, via microneedles, by abrasion, among other forms. In some forms the DNA vaccine is incorporated into liposomes or other forms of nanobodies. In some embodiments, the DNA vaccine includes a delivery system selected from the group consisting of a transfection agent; protamine; a protamine liposome; a polysaccharide particle; a cationic nanoemulsion; a cationic polymer; a cationic polymer liposome; a cationic nanoparticle; a cationic lipid and cholesterol nanoparticle; a cationic lipid, cholesterol, and PEG nanoparticle; a dendrimer nanoparticle. In some embodiments, the DNA vaccines is administered by inhalation or ingestion. In some embodiments, the DNA vaccine is introduced into the blood, the thymus, the pancreas, the skin, the muscle, a tumor, or other sites.

In some embodiments, the compositions disclosed herein are prepared as an RNA vaccine. In some embodiments, the RNA is non-replicating mRNA or virally derived, self-amplifying RNA. In some embodiments, the non-replicating mRNA encodes the peptides disclosed herein and contains 5' and 3' untranslated regions (UTRs). In some embodiments, the virally derived, self-amplifying RNA encodes not only the peptides disclosed herein but also the viral replication machinery that enables intracellular RNA amplification and abundant protein expression. In some embodiments, the RNA is directly introduced into the individual. In some embodiments, the RNA is chemically synthesized or transcribed in vitro. In some embodiments, the mRNA is produced from a linear DNA template using a T7, a T3, or a Sp6 phage RNA polymerase, and the resulting product contains an open reading frame that encodes the peptides disclosed herein, flanking UTRs, a 5' cap, and a poly(A) tail. In some embodiments, various versions of 5' caps are added during or after the transcription reaction using a vaccinia virus capping enzyme or by incorporating synthetic cap or anti-reverse cap analogues. In some embodiments, an optimal length of the poly(A) tail is added to mRNA either directly from the encoding DNA template or by using poly(A) polymerase. The RNA may encode one or more peptides comprising a fragment that is a T cell epitope capable of binding to at least three HLA class I and/or at least three or four HLA class II molecules of a patient. In some embodiments, the fragments are derived from an antigen that is expressed in cancer. In some embodiments, the RNA includes signals to enhance stability and translation. In some embodiments, the RNA also includes unnatural nucleotides to increase the half-life or modified nucleosides to change the immunostimulatory profile.

In some embodiments, the RNAs is introduced by a needle, a gene gun, an aerosol injector, with patches, via microneedles, by abrasion, among other forms. In some forms the RNA vaccine is incorporated into liposomes or other forms of nanobodies that facilitate cellular uptake of RNA and protect it from degradation. In some embodiments, the RNA vaccine includes a delivery system selected from the group consisting of a transfection agent; protamine; a protamine liposome; a polysaccharide particle; a cationic nanoemulsion; a cationic polymer; a cationic polymer liposome; a cationic nanoparticle; a cationic lipid and cholesterol nanoparticle; a cationic lipid, cholesterol, and PEG nanoparticle; a dendrimer nanoparticle; and/or naked mRNA; naked mRNA with in vivo electroporation; protamine-complexed mRNA; mRNA associated with a positively charged oil-in-water cationic nanoemulsion; mRNA associated with a chemically modified dendrimer and complexed with polyethylene glycol (PEG)-lipid; protamine-complexed mRNA in a PEG-lipid nanoparticle; mRNA associated with a cationic polymer such as polyethylenimine (PEI); mRNA associated with a cationic polymer such as PEI and a lipid component; mRNA associated with a polysaccharide (for example, chitosan) particle or gel; mRNA in a cationic lipid nanoparticle (for example, 1,2 dioleoyloxy 3 trimethylammoniumpropane (DOTAP) or dioleoylphosphatidylethanolamine (DOPE) lipids); mRNA complexed with cationic lipids and cholesterol; or mRNA complexed with cationic lipids, cholesterol and PEG-lipid. In some embodiments, the RNA vaccine is administered by inhalation or ingestion. In some embodiments, the RNA is introduced into the blood, the thymus, the pancreas, the skin, the muscle, a tumor, or other sites, and/or by an intradermal, intramuscular, subcutaneous, intranasal, intranodal, intravenous, intrasplenic, intratumoral or other delivery route.

In some embodiments, the polynucleotide or oligonucleotide components are naked nucleotide sequences or be in combination with cationic lipids, polymers or targeting systems. They may be delivered by any available technique. For example, the polynucleotide or oligonucleotide may be introduced by needle injection, preferably intradermally, subcutaneously or intramuscularly. Alternatively, the polynucleotide or oligonucleotide may be delivered directly across the skin using a delivery device such as particle-mediated gene delivery. The polynucleotide or oligonucleotide may be administered topically to the skin, or to mucosal surfaces for example by intranasal, oral, or intrarectal administration.

Uptake of polynucleotide or oligonucleotide constructs may be enhanced by several known transfection techniques, for example those including the use of transfection agents. Examples of these agents include cationic agents, for example, calcium phosphate and DEAE-Dextran and lipofectants, for example, lipofectam and transfectam. The dosage of the polynucleotide or oligonucleotide to be administered can be altered.

The term "treatment" as used herein includes therapeutic and prophylactic treatment. Administration is typically in a "prophylactically effective amount" or a "therapeutically effective amount" (as the case may be, although prophylaxis may be considered therapy), this being sufficient to result in a clinical response or to show clinical benefit to the individual, e.g. an effective amount to prevent or delay onset of the disease or condition, to ameliorate one or more symptoms, to induce or prolong remission, or to delay relapse or recurrence.

The dose may be determined according to various parameters, especially according to the substance used; the age, weight and condition of the individual to be treated; the route of administration; and the required regimen. The amount of antigen in each dose is selected as an amount which induces an immune response. A physician will be able to determine the required route of administration and dosage for any particular individual. The dose may be provided as a single dose or may be provided as multiple doses, for example taken at regular intervals, for example 2, 3 or 4 doses administered hourly. Typically, peptides, polynucleotides or oligonucleotides are typically administered in the range of 1 pg to 1 mg, more typically 1 pg to 10 µg for particle mediated delivery and 1 µg to 1 mg, more typically 1-100 more typically 5-50 µg for other routes. Generally, it is expected that each dose will comprise 0.01-3 mg of antigen. An optimal amount for a particular vaccine can be ascertained by studies involving observation of immune responses in individuals.

In some embodiments, the method of treatment comprises administration to an individual of more than one peptide, polynucleic acid or vector. These may be administered together/simultaneously and/or at different times or sequentially. The use of combinations of different peptides, optionally targeting different antigens, may be important to overcome the challenges of viral heterogeneity and HLA heterogeneity of individuals. The use of peptides of the disclosure in combination expands the group of individuals who can experience clinical benefit from vaccination. Multiple pharmaceutical compositions, manufactured for use in one regimen, may define a drug product. In some cases, different peptides, polynucleic acids or vectors of a single treatment may be administered to the individual within a period of, for example, 1 year, or 6 months, or 3 months, or 60 or 50 or 40 or 30 days.

Routes of administration include but are not limited to intranasal, oral, subcutaneous, intradermal, and intramuscular. The subcutaneous administration is particularly preferred. Subcutaneous administration may for example be by injection into the abdomen, lateral and anterior aspects of upper arm or thigh, scapular area of back, or upper ventrodorsal gluteal area.

In some embodiments, the compositions of the disclosure are administered in one, or more doses, as well as, by other routes of administration. For example, such other routes include, intracutaneously, intravenously, intravascularly, intraarterially, intraperitnoeally, intrathecally, intratracheally, intracardially, intralobally, intramedullarly, intrapulmonarily, and intravaginally. Depending on the desired duration of the treatment, the compositions according to the disclosure may be administered once or several times, also intermittently, for instance on a monthly basis for several months or years and in different dosages.

Solid dosage forms for oral administration include capsules, tablets, caplets, pills, powders, pellets, and granules. In such solid dosage forms, the active ingredient is ordinarily combined with one or more pharmaceutically acceptable excipients, examples of which are detailed above. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

In some embodiments, the compositions of the disclosure are administered, or the methods and uses for treatment according to the disclosure are performed, alone or in combination with other pharmacological compositions or treatments, for example other immunotherapy, vaccine or anti-virals. In some embodiments, the other therapeutic compositions or treatments are administered either simultaneously or sequentially with (before or after) the composition(s) or treatment of the disclosure.

In some embodiments, the method of treatment is a method of vaccination or a method of providing immunotherapy. As used herein, "immunotherapy" is the treatment of a disease or condition by inducing or enhancing an immune response in an individual. In certain embodiments, immunotherapy refers to a therapy that comprises the administration of one or more drugs to an individual to elicit T cell responses. In a specific embodiment, immunotherapy refers to a therapy that comprises the administration or expression of polypeptides that contain one or more PEPIs to an individual to elicit a T cell response to recognize and kill cells that display the one or more PEPIs on their cell surface in conjunction with a class I HLA. In another embodiment, immunotherapy refers to a therapy that comprises the administration or expression of polypeptides that contain one or more PEPIs presented by class II HLAs to an individual to elicit a T helper response to provide co-stimulation to cytotoxic T cells that recognize and kill diseased cells that display the one or more PEPIs on their cell surface in conjunction with a class I HLAs. In still another specific embodiment, immunotherapy refers to a therapy that comprises administration of one or more drugs to an individual that re-activate existing T cells to kill target cells and/or virus.

EXAMPLES

Example 1—PolyPEPI-SCoV-2 Vaccine Design

The SARS-CoV genome has a size of ~30 kilobases which, like other coronaviruses, encodes for multiple structural and non-structural proteins. The structural proteins include the spike (S) protein, the envelope (E) protein, the membrane (M) protein, and the nucleocapsid (N) protein.

The PolyPEPI-SCoV-2 vaccine disclosed herein is composed of one or more 30 amino acid long peptides capable of inducing positive, desirable T cell (both CD8 cytotoxic and CD4 helper) responses and B cell mediated antibody responses against one or more, and preferably all 4 of the structural viral antigens in a high proportion of individuals in the global population.

A total of 19 whole genome sequences of COVID-19 were downloaded on 28 Mar. 2020 from the NCBI database. (ncbi.nm.nih.gov/genome/genomes/86693)

The accession IDs are the following: NC_045512.2, MN938384.1, MN975262.1, MN985325.1, MN988713.1, MN994467.1, MN994468.1, MN997409.1, MN988668.1, MN988669.1, MN996527.1, MN996528.1, MN996529.1, MN996530.1, MN996531.1, MT135041.1, MT135043.1, MT027063.1, MT027062.1. The first ID represents the GenBank reference sequence. Four structural protein sequences (Surface glycoprotein, Envelope protein, Membrane glycoprotein, Nucleocapsid phosphoprotein) of translated coding sequences were aligned and compared with a multiple sequence alignment. Of the 19 sequences 15 were completely the same. However, we obtained single amino acid changes in 4 nucleocapsid proteins. These replacements are the following: MN988713.1: Nucleocapsid 194 S→X, MT135043.1: Nucleocapsid 343 D→V, MT027063.1: Nucleocapsid 194 S→L, MT027062.1: Nucleocapsid 194 S→L. None of these changes affected the epitopes that have been selected for targets in the present vaccine polypeptides.

Seventeen peptide fragments were selected from the conserved regions of the presently known viral antigen sequences for SARS-CoV-2 structural proteins. The fragments were selected to maximize multi-HLA class I-binding PEPI3+ and multi-HLA class II-binding PEPI4+, i.e. shared personal epitopes, in a model population. The peptides were also designed to incorporate linear B cell epitopes. Specifically, 9mer sequences in the conserved regions of the four target antigens that are PEPI2+ in the highest proportion of individuals in the model population were selected. These 9mers were extended to incorporate nearby linear B-cell epitopes in the conserved sequence of the target antigens. 30mer fragments of the target antigens that incorporate both the 9mer "bestEPIs" and linear B cell epitopes were then selected to maximize the proportion of individuals in the model population having a HLA class II-binding PEPI4+ in the 30mer fragment. The model population comprises ~16,000 HLA-genotyped individuals obtained from a bone-marrow transplant biobank, with about 1,000 individuals from each of 16 different ethnic groups. The sequences of the selected 30 mer peptide fragments and HLA class I-binding epitopes that are PEPI3+ and HLA class II-binding epitopes that are PEPI4+ in the highest proportion of individuals in the model population are shown in Table 2A.

TABLE 2A

List of PolyPEPI-SCoV-2 peptide sequences. Bold: 9mer HLAI bestEPI sequences, underlined: 15mer bestEPI sequences.

| SEQ ID no. | TREOS ID | COVID-19 pos. | Peptide (30mer) | HLAI (CD8) | HLAII (CD4) | HLAII (CD4, P3) |
|---|---|---|---|---|---|---|
| 1 | CORONA-01 | Surface(22-51) | TQLPPAYTNSFTRGVYYPDKVFRSSVLHST | 68% | 41% | 78% |
| 2 | CORONA-02 | Surface(35-64) | GVYYPDKVFRSSVLHSTQDLFLPFFSNVTW | 71% | 94% | 99% |
| 3 | CORONA-03 | Surface(76-105) | TKRFDNPVLPFNDGVYFASTEKSNIIRGWI | 46% | 12% | 24% |
| 4 | CORONA-04 | Surface(98-127) | SNIIRGWIFGTTLDSKTQSLLIVNNATNVV | 52% | 28% | 57% |
| 5 | CORONA-05 | Surface(253-282) | DSSSGWTAGAAAYYVGYLQPRTFLLKYNEN | 84% | 97% | 100% |
| 6 | CORONA-06 | Surface(391-420) | CFTNVYADSFVIRGDEVRQIAPGQTGKIAD | 57% | 40% | 73% |
| 7 | CORONA-07 | Surface(683-712) | RARSVASQSIIAYTMSLGAENSVAYSNNSI | 70% | 61% | 87% |
| 8 | CORONA-08 | Surface(701-730) | AENSVAYSNNSIAIPTNFTISVTTEILPVS | 62% | 33% | 57% |
| 9 | CORONA-09 | Surface(893-922)* | ALQIPFAMQMAYRFNGIGVTQNVLYENQKL | 93% | 99% | 100% |
| 10 | CORONA-10 | Surface(898-927)* | FAMQMAYRFNGIGVTQNVLYENQKLIANQF | 89% | 45% | 81% |
| 11 | CORONA-11 | Surface(1091-1120) | REGVFVSNGTHWFVTQRNFYEPQIITTDNT | 67% | 51% | 87% |
| 12 | CORONA-12 | Nucleocapsid(36-65)* | RSKQRRPQGLPNNTASWFTALTQHGKEDLK | 36% | 36% | 66% |
| 13 | CORONA-13 | Nucleocapsid(255-284)* | SKKPRQKRTATKAYNVTQAFGRRGPEQTQG | 48% | 22% | 48% |
| 14 | CORONA-14 | Nucleocapsid(290-319)* | ELIRQGTDYKHWPQIAQFAPSASAFFGMSR | 54% | 50% | 76% |
| 15 | CORONA-15 | Nucleocapsid(384-413)* | QRQKKQQTVTLLPAADLDDFSKQLQQSMSS | 23% | 36% | 70% |
| 16 | CORONA-16 | Membrane(93-122) | LSYFIASFRLFARTRSMWSFNPETNILLNV | 90% | 100% | 100% |
| 17 | CORONA-17 | Envelope(45-74) | NIVNVSLVKPSFVYSRVKNLNSSRVPDLL | 46% | 100% | 100% |

*B cell epitope containing peptides, B cell epitopes are listed in Table 2B

TABLE 2B

Linear B cell epitopes

| SEQ ID No | TREOS ID | Corona virus part | IEDB ID | B cell epitopes SEQ |
|---|---|---|---|---|
| 18 | CORONA-09 | Surface(893-922) | 3176 | AMQMAYRF |
| 19 | CORONA-10 | Surface(898-927) | 3176 | AMQMAYRF |
| 20 | CORONA-12 | Nucleocapsid(36-65) | 55683 | RRPQGLPNNTASWFT |
| 21 | | | 21065 | GLPNNTASWFTALTQHGK |
| 22 | CORONA-12 | Nucleocapsid(36-65) | 55683 | RRPQGLPNNTASWFT |
| 23 | | | 21065 | GLPNNTASWFTALTQHGK |
| 24 | CORONA-14 | Nucleocapsid(290-319) | 28371 | IRQGTDYKHWPQIAQFA |
| 25 | | | 31166 | KHWPQIAQFAPSASAFF |
| 26 | | | 50965 | QGTDYKHW |
| 27 | CORONA-15 | Nucleocapsid(384-413) | 37640 | LLPAAD |

Reference: Preliminary Identification of Potential Vaccine Targets for the COVID-19 Coronavirus (SARS-CoV-2) Based on SARS-CoV Immunological Studies. Table 4. SARS-CoV-derived linear B cell epitopes from S (23; 20 of which are located in subunit S2) and N (22) proteins that are identical in SARS-CoV-2 (45 epitopes in total).

TABLE 2C

Helper table for Best HLAI and HLAII PEPIs:

| TREOSID | SEQ ID NO: | Best HLAI | SEQ ID NO: | Best HLAII |
|---|---|---|---|---|
| CORONA-01 | 28 | YTNSFTRGV | 44 | YYPDKVFRSSVLHST |
| CORONA-02 | 29 | STQDLFLPF | 45 | STQDLFLPFFSNVTW |
| CORONA-03 | 30 | RFDNPVLPF | 46 | DGVYFASTEKSNIIR |
| CORONA-04 | 31 | IVNNATNVV | 47 | KTQSLLIVNNATNVV |
| CORONA-05 | 32 | YLQPRTFLL | 48 | AAAYYVGYLQPRTFL |
| CORONA-06 | 33 | NVYADSFVI | 49 | CFTNVYADSFVIRGD |
| CORONA-07 | 34 | SIIAYTMSL | 50 | SQSIIAYTMSLGAEN |
| CORONA-08 | 35 | FTISVTTEI | 51 | TNFTISVTTEILPVS |
| CORONA-09 | 36 | FAMQMAYRF | 52 | ALQIPFAMQMAYRFN |
| CORONA-10 |  |  | 53 | FAMQMAYRFNGIGVT |
| CORONA-11 | 37 | FVSNGTHWF | 54 | HWFVTQRNFYEPQII |
| CORONA-12 | 38 | NTASWFTAL | 55 | NNTASWFTALTQHGK |
| CORONA-13 | 39 | KAYNVTQAF | 56 | TATKAYNVTQAFGRR |
| CORONA-14 | 40 | FAPSASAFF | 57 | QIAQFAPSASAFFGM |
| CORONA-15 | 41 | FSKQLQQSM | 58 | KKQQTVTLLPAADLD |
| CORONA-16 | 42 | RLFARTRSM | 59 | LSYFIASFRLFARTR |
| CORONA-17 | 43 | YVYSRVKNL | 60 | KPSFYVYSRVKNLNS |

Example 2—Comparison of PolyPEPI-SCoV-2 and State of Art Vaccine

As suggested in the article "Preliminary Identification of Potential Vaccine Targets for the COVID-19 Coronavirus (SARS-CoV-2) Based on SARS-CoV Immunological Studies" (Ahmed et al), we modelled the possible efficacy (immunogenicity) of a vaccine based on the targets identified therein. The result was compared to a selection of PolyPEPI-SCov-2 vaccine peptides as described herein.

SF Ahmed et al identified 61 T-cell epitopes associated with 19 HLAI alleles to provide estimated accumulated population coverage of 96.29% based on global allele frequencies. (Ahmed et al. Viruses, 12(3). 2020) The following T-cell epitopes shown in Table 3 were suggested as potential targets for a vaccine (Table 3 of the article; 2 of 61 were only 8 mer epitopes, we excluded from the simulation).

TABLE 3

Adopted from SF Ahmed et al: Set of the SARS-CoV-derived spike (S) and nucleocapsid (N) protein T cell epitopes (obtained from positive MHC binding assays) that are identical in SARS-CoV-2 and that maximize estimated population coverage globally.

| HLA Allele | Global Accumulated Population Coverage2 (%) | Accumulated Population Coverage in China (%) | SEQ ID NO: | Epitopes |
|---|---|---|---|---|
| HLA-A*02:01 | 39.08 | 14.62 | 61 | FIAGLIAIV |
|  |  |  | 62 | GLIAIVMVTI |
|  |  |  | 63 | IITTDNTFV |
|  |  |  | 64 | ALNTLVKQL |
|  |  |  | 65 | LITGRLQSL |
|  |  |  | 66 | LLLQYGSFC |
|  |  |  | 67 | LQYGSFCT |
|  |  |  | 68 | NLNESLIDL |
|  |  |  | 69 | RLDKVEAEV |
|  |  |  | 70 | RLNEVAKNL |
|  |  |  | 71 | RLQSLQTYV |
|  |  |  | 72 | VLNDILSRL |
|  |  |  | 73 | VVFLHVTYV |
|  |  |  | 74 | ILLNKHID |
|  |  |  | 75 | FPRGQGVPI |
|  |  |  | 76 | LLLLDRLNQ |
|  |  |  | 77 | GMSRIGMEV |
|  |  |  | 78 | ILLNKHIDA |
|  |  |  | 79 | ALNTPKDHI |
|  |  |  | 80 | LALLLLDRL |
|  |  |  | 81 | LLLDRLNQL |
|  |  |  | 82 | LLLLDRLNQL |
|  |  |  | 83 | LQLPQGTTL |
|  |  |  | 84 | AQFAPSASA |
|  |  |  | 85 | TTLPKGFYA |
|  |  |  | 86 | VLQLPQGTTL |
| HLA-A*24:02 | 55.48 | 36.11 | 87 | GYQPYRVVVL |
|  |  |  | 88 | PYRVVVLSF |
|  |  |  | 89 | LSPRWYFYY |

TABLE 3-continued

Adopted from SF Ahmed et al: Set of the SARS-CoV-derived spike (S) and nucleocapsid (N) protein T cell epitopes (obtained from positive MHC binding assays) that are identical in SARS-CoV-2 and that maximize estimated population coverage globally.

| HLA Allele | Global Accumulated Population Coverage2 (%) | Accumulated Population Coverage in China (%) | SEQ ID NO: | Epitopes |
|---|---|---|---|---|
| HLA-A*01:01 | 66.78 | 39.09 | 90 | DSFKEELDKY |
|  |  |  | 91 | LIDLQELGKY |
|  |  |  | 88 | PYRVVVLSF |
|  |  |  | 92 | GTTLPKGFY |
|  |  |  | 93 | VTPSGTWLTY |
| HLA-A*03:01 | 76.14 | 41.68 | 94 | GSFCTQLNR |
|  |  |  | 95 | GVVFLHVTY |
|  |  |  | 96 | AQALNTLVK |
|  |  |  | 97 | MTSCCSCLK |
|  |  |  | 98 | ASANLAATK |
|  |  |  | 99 | SLIDLQELGK |
|  |  |  | 100 | SVLNDILSR |
|  |  |  | 101 | TQNVLYENQK |
|  |  |  | 102 | CMTSCCSCLK |
|  |  |  | 103 | VQIDRLITGR |
|  |  |  | 104 | KTFPPTEPK |
|  |  |  | 105 | KTFPPTEPKK |
|  |  |  | 89 | LSPRWYFYY |
|  |  |  | 106 | ASAFFGMSR |
|  |  |  | 107 | ATEGALNTPK |
|  |  |  | 108 | QLPQGTTLPK |
|  |  |  | 109 | QQQGQTVTK |
|  |  |  | 110 | QQQQGQTVTK |
|  |  |  | 111 | SASAFFGMSR |
|  |  |  | 112 | SQASSRSSSR |
|  |  |  | 113 | TPSGTWLTY |
| HLA-A*11:01 | 83.39 | 73.43 | 94 | GSFCTQLNR |
|  |  |  | 95 | GVVFLHVTY |
|  |  |  | 96 | AQALNTLVK |
|  |  |  | 97 | MTSCCSCLK |
|  |  |  | 98 | ASANLAATK |
|  |  |  | 99 | SLIDLQELGK |
|  |  |  | 100 | SVLNDILSR |
|  |  |  | 101 | TQNVLYENQK |
|  |  |  | 102 | CMTSCCSCLK |
|  |  |  | 103 | VQIDRLITGR |
|  |  |  | 104 | KTFPPTEPK |
|  |  |  | 105 | KTFPPTEPKK |
|  |  |  | 89 | LSPRWYFYY |
|  |  |  | 106 | ASAFFGMSR |
|  |  |  | 107 | ATEGALNTPK |
|  |  |  | 108 | QLPQGTTLPK |
|  |  |  | 109 | QQQGQTVTK |
|  |  |  | 110 | QQQQGQTVTK |
|  |  |  | 111 | SASAFFGMSR |
|  |  |  | 112 | SQASSRSSSR |
|  |  |  | 113 | TPSGTWLTY |
| HLA-A*68:01 | 85.71 | 74.25 | 94 | GSFCTQLNR |
|  |  |  | 95 | GVVFLHVTY |
|  |  |  | 96 | AQALNTLVK |
|  |  |  | 97 | MTSCCSCLK |
|  |  |  | 98 | ASANLAATK |
|  |  |  | 99 | SLIDLQELGK |
|  |  |  | 100 | SVLNDILSR |
|  |  |  | 101 | TQNVLYENQK |
|  |  |  | 102 | CMTSCCSCLK |
|  |  |  | 103 | VQIDRLITGR |
|  |  |  | 104 | KTFPPTEPK |
|  |  |  | 105 | KTFPPTEPKK |
|  |  |  | 89 | LSPRWYFYY |
|  |  |  | 106 | ASAFFGMSR |
|  |  |  | 107 | ATEGALNTPK |
|  |  |  | 108 | QLPQGTTLPK |
|  |  |  | 109 | QQQGQTVTK |
|  |  |  | 110 | QQQQGQTVTK |
|  |  |  | 111 | SASAFFGMSR |

TABLE 3-continued

Adopted from SF Ahmed et al: Set of the SARS-CoV-derived spike (S) and nucleocapsid (N) protein T cell epitopes (obtained from positive MHC binding assays) that are identical in SARS-CoV-2 and that maximize estimated population coverage globally.

| HLA Allele | Global Accumulated Population Coverage2 (%) | Accumulated Population Coverage in China (%) | SEQ ID NO: | Epitopes |
|---|---|---|---|---|
| | | | 112 | SQASSRSSSR |
| | | | 113 | TPSGTWLTY |
| HLA-A*23:01 | 87.72 | 74.87 | 87 | GYQPYRVVVL |
| | | | 88 | PYRVVVLSF |
| | | | 89 | LSPRWYFYY |
| HLA-A*31:01 | 89.55 | 76.93 | 94 | GSFCTQLNR |
| | | | 95 | GVVFLHVTY |
| | | | 96 | AQALNTLVK |
| | | | 97 | MTSCCSCLK |
| | | | 98 | ASANLAATK |
| | | | 99 | SLIDLQELGK |
| | | | 100 | SVLNDILSR |
| | | | 101 | TQNVLYENQK |
| | | | 102 | CMTSCCSCLK |
| | | | 103 | VQIDRLITGR |
| | | | 104 | KTFPPTEPK |
| | | | 105 | KTFPPTEPKK |
| | | | 89 | LSPRWYFYY |
| | | | 106 | ASAFFGMSR |
| | | | 107 | ATEGALNTPK |
| | | | 108 | QLPQGTTLPK |
| | | | 109 | QQGGQTVTK |
| | | | 110 | QQQQGQTVTK |
| | | | 111 | SASAFFGMSR |
| | | | 112 | SQASSRSSSR |
| | | | 113 | TPSGTWLTY |
| HLA-B*07:02 | 90.89 | 77.61 | 114 | FPNITNLCPF |
| | | | 115 | APHGVVFLHV |
| | | | 75 | FPRGQGVPI |
| | | | 116 | APSASAFFGM |
| HLA-B*08:01 | 92.85 | 78.41 | 75 | FPRGQGVPI |
| HLA-B*35:01 | 93.53 | 79.23 | 114 | FPNITNLCPF |
| | | | 115 | APHGVVFLHV |
| | | | 75 | FPRGQGVPI |
| | | | 116 | APSASAFFGM |
| HLA-B*15:01 | 94.18 | 82.26 | 117 | LQIPFAMQM |
| | | | 118 | RVDFCGKGY |
| HLA-B*51:01 | 94.72 | 83.73 | 114 | FPNITNLCPF |
| | | | 115 | APHGVVFLHV |
| | | | 75 | FPRGQGVPI |
| | | | 116 | APSASAFFGM |
| HLA-B*18:01 | 95.23 | 83.88 | 119 | YEQYIKWPWY |
| HLA-B*27:05 | 95.55 | 84 | 120 | GRLQSLQTY |
| | | | 118 | RVDFCGKGY |
| | | | 121 | VRFPNITNL |
| HLA-A*33:01 | 95.79 | 85.28 | 97 | MTSCCSCLK |
| | | | 99 | SLIDLQELGK |
| | | | 102 | CMTSCCSCLK |
| | | | 103 | VQIDRLITGR |
| | | | 111 | SASAFFGMSR |
| | | | 112 | SQASSRSSSR |
| HLA-B*58:01 | 95.99 | 86.45 | 117 | LQIPFAMQM |
| | | | 118 | RVDFCGKGY |
| HLA-C*15:02 | 96.17 | 87.22 | 117 | LQIPFAMQM |
| | | | 118 | RVDFCGKGY |
| HLA-C*14:02 | 96.29 | 88.11 | 121 | VRFPNITNL |

Ahmed et al suggest that the estimated maximum population coverage might be achieved by selecting at least one epitope for each listed HLA allele (i.e. 19 sequences). Accordingly, we made a random selection from this T-cell epitope set, selecting one epitope for each HLA allele (exactly as suggested by the authors). Because these are promiscuous HLA-binding epitopes, therefore sometimes we selected the same epitope for more than one HLA allele. This was repeated 30 times and the selected epitopes were compared to 10 peptides selected for PolyPEPI-SCoV2 (SEQ ID NOs: 2, 5, 7, 9, 12, 13, 14, 15, 16, 17). The in-silico comparison was performed on our ~16,000 HLA-genotyped individuals database obtained from a bone-marrow transplant biobank. Our database contains data from 16 ethnic groups (about 1,000 individuals per group). We computed the proportion of individuals with CD8+ immune response against at least one epitope. The worldwide (global) coverage of the PolyPEPI-SCoV2 is 99.8%, compared to the simulated vaccine (random epitope selection), where the average coverage was 61% (±9.9%), for some of the ethnic groups (e.g. Caucasians) achieving lower protection than for others (e.g. Japanese) (FIG. 1).

Figure 2:
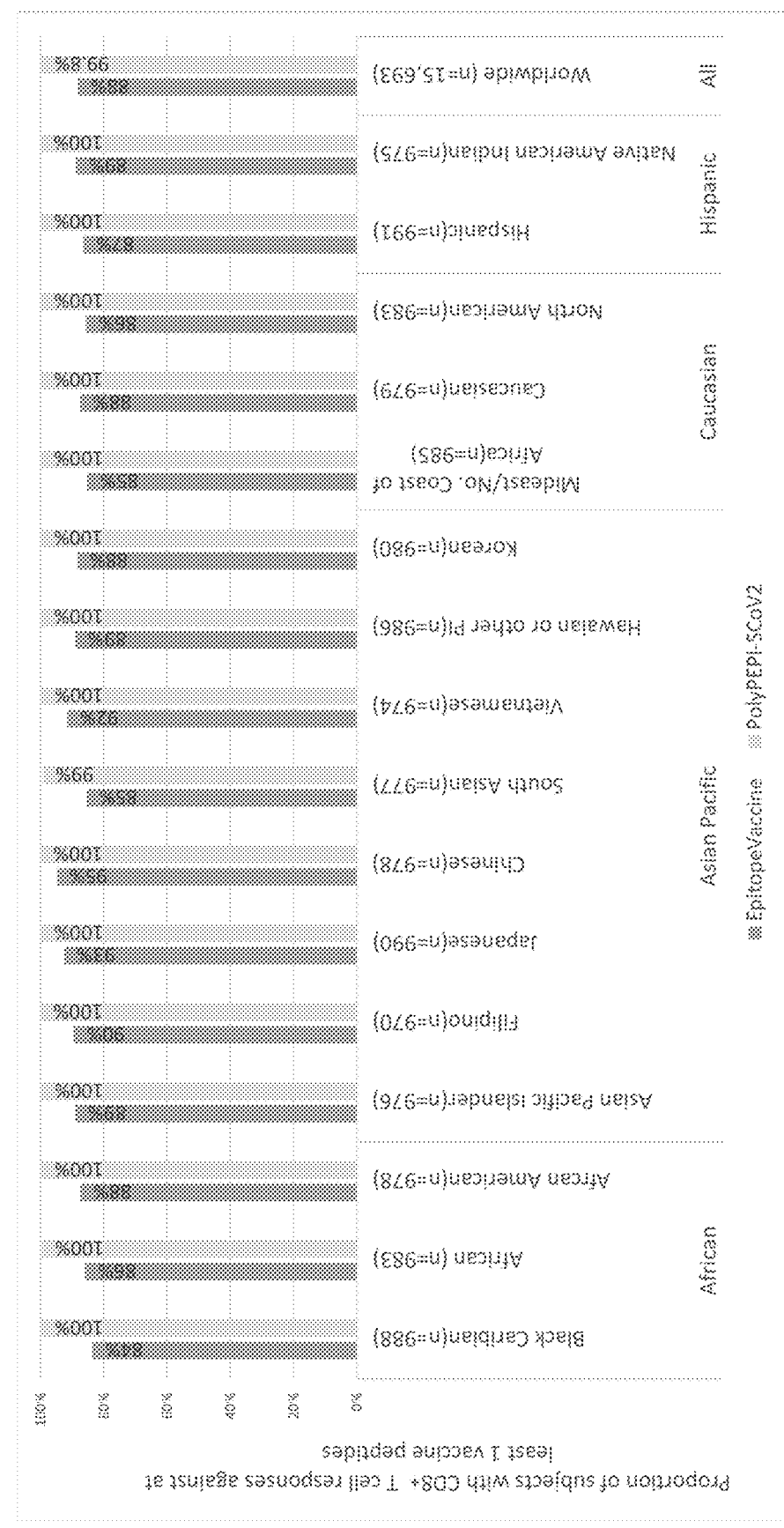
FIG. 2. Comparison of predicted vaccine induced immune response rates (CD8) for all 59 peptides selected by SF Ahmed et al. or 10 peptides of PolyPEPI-SCoV2 vaccine in ~16,000 individuals of 16 ethnicities.

A further special (not practical) situation was modelled, where all T-cell epitopes listed in Ahmed et al (n=59) were selected into the vaccine. In this case the worldwide coverage increased to up to 88% but still not reaching the level of PolyPEPI-SCoV2 (FIG. 2). This showed uniform coverage between the ethnic groups also for the Epitope vaccine.

Figure 3:
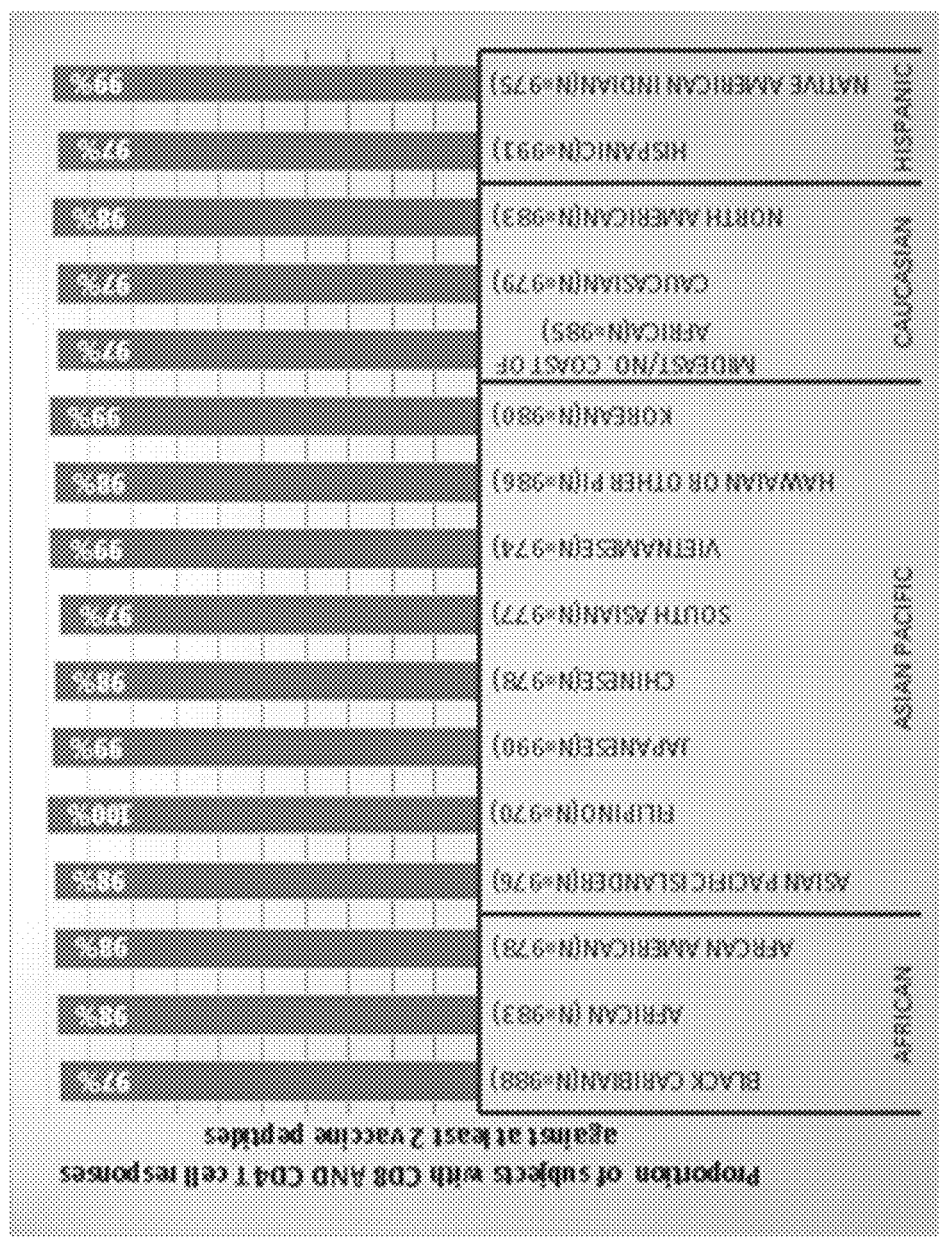
FIG. 3. Proportion of individuals having both CD4 and CD8 T cells against at least 2 peptides of PolyPEPI-SCoV2 vaccine. Prediction was performed in the ~16,000 individual cohort of 16 ethnicities.

We also modelled the ability of the PolyPEPI-SCoV2 vaccine (same 10 peptides selected) to induce HLA class II restricted CD4 responses (HLA class II PEPIs) in addition to CD8 response (FIG. 3). In each ethnic cohort at least 97% of the individuals elicited both CD8 and CD4 T cell responses against at least 2 peptides of the PolyPEPI-SCoV2 vaccine.

Example 3—Comparison of Number of Immunogenic Epitopes of PolyPEPI-SCoV-2 and State of Art Peptide Vaccine Based on the previous dataset derived from Ahmed et al, we computed the number of immunogenic epitopes in each individual in the model population. The distribution of this number shows the strengths of the vaccine against potential mutations.

Figure 4:
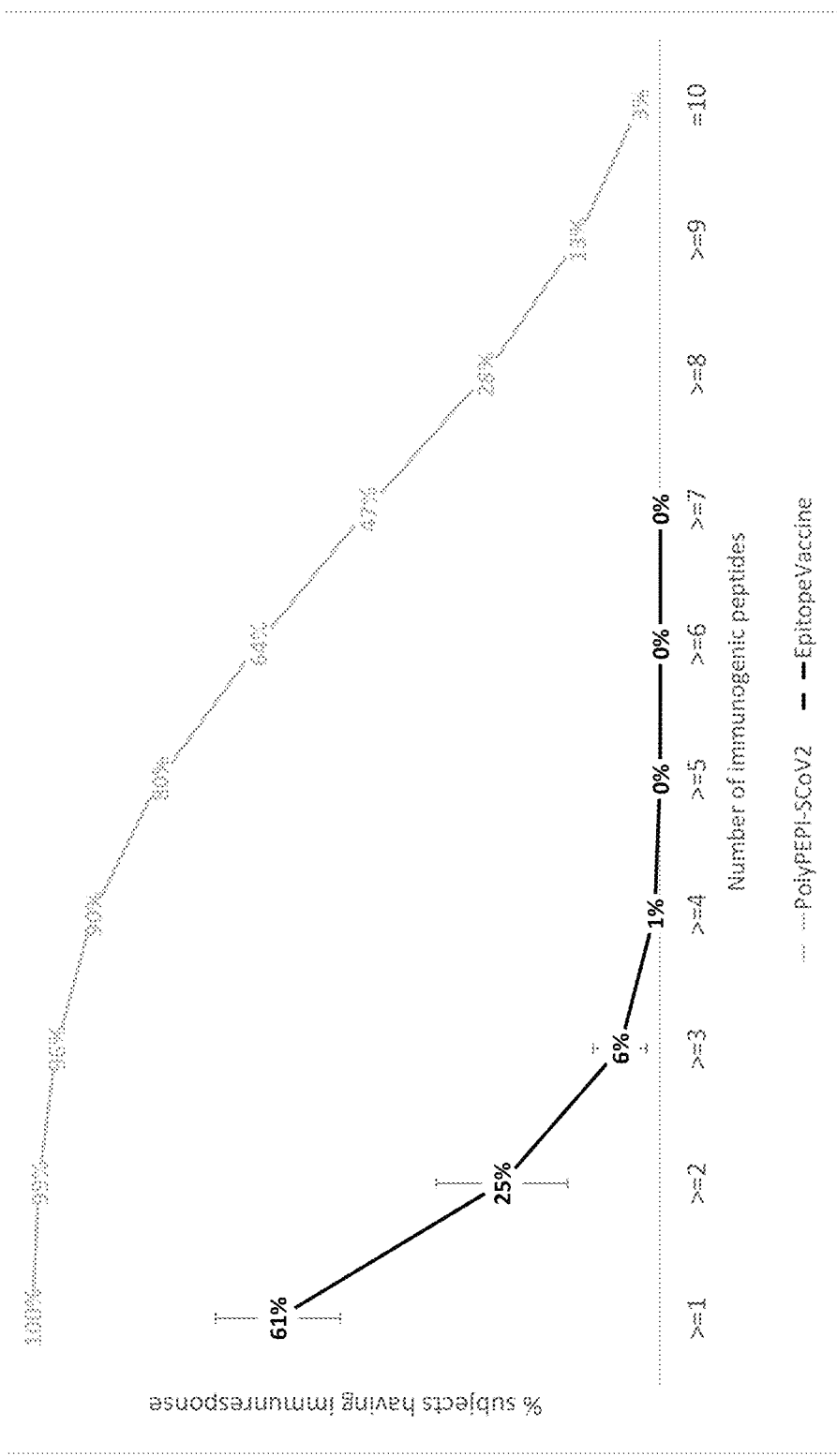
FIG. 4. Proportion of individuals (in the ~16,000 cohort) having immune response against ≥1-10 vaccine epitopes induced by randomly selected Epitope Vaccine proposed by SF Ahmed et al. and 10 peptides of PolyPEPI-SCoV2 vaccine.

FIG. 4 shows that 61% (±9.9%) of the individuals have immune response against at least one of the vaccine's epitopes, but only 25% (±10.4%) of the individuals have response against at least 2 epitopes from 19. This means, if the virus is mutated on one particular epitope, the other epitope still can generate immune response (for a fraction of individuals). In contrast, 99% of the model population treated with PolyPEPI-SCoV2 have response against at least 2 epitopes. The gap is even bigger for at least 3 target epitopes (96% for PolyPEPI-SCov2 vs. 6% for EpitopeVaccine).

Figure 5:
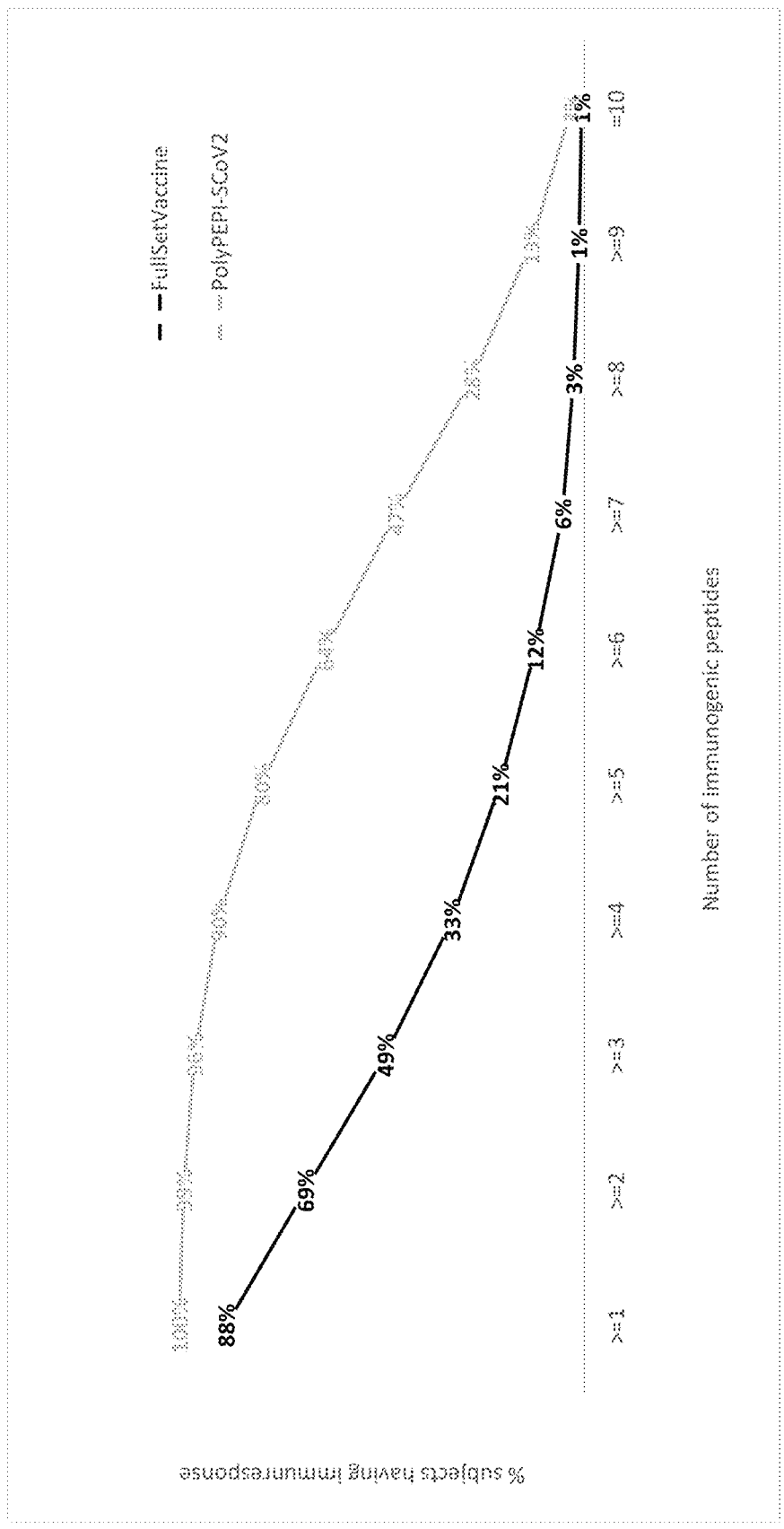
FIG. 5. Proportion of individuals (in the ~16,000 cohort) having immune response against ≥1-10 vaccine epitopes induced by all 59 peptides of the Epitope Vaccine proposed by SF Ahmed et al. or the 10 peptides of PolyPEPI-SCoV2 vaccine.

For the vaccine containing all 59 epitopes the situation would be somewhat better: 69% of individuals can have immune response against 2 or more epitopes (FIG. 5), but this is still a smaller proportion of the population compared with PolyPEPI-SCoV2 vaccine (10 peptides).

Example 4

Modelling of COVID-19 infection and projections warn of rapid evolution which could undermine attempts to vaccinate against and treat infection. There is an urgent need to project how transmission of the novel Beta-coronavirus SARS-CoV-2 will unfold in coming years. These dynamics will depend on seasonality, the duration of immunity, and the strength of cross-immunity to/from the other human coronaviruses. Using data from the United States, the inventors measured how these factors affect transmission of human coronaviruses HCoV-OC43 and HCoV-HKU1. (Kissler et al. 2020 doi.org/10.1101/2020.03.04.20031112). The design of the vaccine peptides and compositions described herein are robust to rapid virus evolution and cover global population by the selection of multiple immunogenic but conserved sequences, preferably derived from multiple structural proteins.

It is anticipated that as the virus continues to evolve and as more data is collected, additional mutations will be observed. Such mutations will not affect the global coverage of the polypeptides and multi-peptide vaccine described herein, provided that mutations occur outside of the identified epitope regions. Even if mutations do occur within any of the epitope regions selected, then the remaining immunogenic epitopes still provide robust protection against the virus, since the majority of individuals will retain a broad repertoire of virus-specific memory T cell clones, For example, for the ten peptide vaccine comprising polypeptides of SEQ ID NOs: 2, 5, 7, 9, 12, 13, 14, 15, 16, and 17, 94% of patients are predicted to have immune responses against at least 3 vaccine peptides and 85% and 71% against 4 and 5 peptides, respectively.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

Full length SARS-CoV-2 structural protein sequences

Surface glycoprotein alias Spike 1273 aa NCBI Reference Sequence: YP_009724390.1

(SEQ ID NO: 122)

MFVFLVLLPLVSSQCVNLTTRTQLPPAYTNSFTRGVYYPDKVFRSSVLHS

TQDLFLPFFSNVTWFHAIHVSGTNGTKRFDNPVLPFNDGVYFASTEKSNI

IRGWIFGTTLDSKTQSLLIVNNATNVVIKVCEFQFCNDPFLGVYYHKNNK

SWMESEFRVYSSANNCTFEYVSQPFLMDLEGKQGNFKNLREFVFKNIDGY

FKIYSKHTPINLVRDLPQGFSALEPLVDLPIGINITRFQTLLALHRSYLT

PGDSSSGWTAGAAAYYVGYLQPRTFLLKYNENGTITDAVDCALDPLSETK

CTLKSFTVEKGIYQTSNFRVQPTESIVRFPNITNLCPFGEVFNATRFASV

YAWNRKRISNCVADYSVLYNSASFSTFKCYGVSPTKLNDLCFTNVYADSF

VIRGDEVRQIAPGQTGKIADYNYKLPDDFTGCVIAWNSNNLDSKVGGNYN

YLYRLFRKSNLKPFERDISTEIYQAGSTPCNGVEGFNCYFPLQSYGFQPT

NGVGYQPYRVVVLSFELLHAPATVCGPKKSTNLVKNKCVNFNFNGLTGTG

VLTESNKKFLPFQQFGRDIADTTDAVRDPQTLEILDITPCSFGGVSVITP

GTNTSNQVAVLYQDVNCTEVPVAIHADQLTPTWRVYSTGSNVFQTRAGCL

-continued

| Full length SARS-CoV-2 structural protein sequences |
|---|
| IGAEHVNNSYECDIPIGAGICASYQTQTNSPRRARSVASQSITAYTMSLG |
| AENSVAYSNNSIAIPTNFTISVTTEILPVSMTKTSVDCTMYICGDSTECS |
| NLLLQYGSFCTQLNRALTGIAVEQDKNTQEVFAQVKQTYKTPPIKDFGGF |
| NFSQILPDPSKPSKRSFIEDLLFNKVTLADAGFIKQYGDCLGDIAARDLI |
| CAQKFNGLTVLPPLLTDEMIAQYTSALLAGTITSGWTFGAGAALQIPFAM |
| QMAYRFNGIGVTQNVLYENQKLIANQFNSAIGKIQDSLSSTASALGKLQD |
| VVNQNAQALNTLVKQLSSNFGAISSVLNDILSRLDKVEAEVQIDRLITGR |
| LQSLQTYVTQQLIRAAEIRASANLAATKMSECVLGQSKRVDFCGKGYHLM |
| SFPQSAPHGVVFLHVTYVPAQEKNFTTAPAICHDGKAHFPREGVFVSNGT |
| HWFVTQRNFYEPQIITTDNTFVSGNCDVVIGIVNNTVYDPLQPELDSFKE |
| ELDKYFKNHTSPDVDLGDISGINASVVNIQKEIDRLNEVAKNLNESLIDL |
| QELGKYEQYIKWPWYIWLGFIAGLIAIVMVTIMLCCMTSCCSCLKGCCSC |
| GSCCKFDEDDSEPVLKGVKLHYT |
| Nucleocapsid phosphoprotein 419 aa NCBI Reference Sequence: YP_009724397.2 (SEQ ID NO: 123) |
| MSDNGPQNQRNAPRITFGGPSDSTGSNQNGERSGARSKQRRPQGLPNNTA |
| SWFTALTQHGKEDLKFPRGQGVPINTNSSPDDQIGYYRRATRRIRGGDGK |

-continued

| Full length SARS-CoV-2 structural protein sequences |
|---|
| MKDLSPRWYFYYLGTGPEAGLPYGANKDGIIWVATEGALNTPKDHIGTRN |
| PANNAAIVLQLPQGTTLPKGFYAEGSRGGSQASSRSSSRSRNSSRNSTPG |
| SSRGTSPARMAGNGGDAALALLLLDRLNQLESKMSGKGQQQQGQTVTKKS |
| AAEASKKPRQKRTATKAYNVTQAFGRRGPEQTQGNFGDQELIRQGTDYKH |
| WPQIAQFAPSASAFFGMSRIGMEVTPSGTWLTYTGAIKLDDKDPNFKDQV |
| ILLNKHIDAYKTFPPTEPKKDKKKKADETQALPQRQKKQQTVTLLPAADL |
| DDFSKQLQQSMSSADSTQA |
| Envelope protein 75 aa NCBI Reference Sequence: YP_009724392.1 (SEQ ID NO: 124) |
| MYSFVSEETGTLIVNSVLLFLAFVVFLLVTLAILTALRLCAYCCNIVNVS |
| LVKPSFYVYSRVKNLNSSRVPDLLV |
| Membrane glycoprotein 222 aa NCBI Reference Sequence: YP_009724393.1 (SEQ ID NO: 125) |
| MADSNGTITVEELKKLLEQWNLVIGFLFLTWICLLQFAYANRNRFLYIIK |
| LIFLWLLWPVTLACFVLAAVYRINWITGGIAIAMACLVGLMWLSYFIASF |
| RLFARTRSMWSFNPETNILLNVPLHGTILTRPLLESELVIGAVILRGHLR |
| IAGHHLGRCDIKDLPKEITVATSRTLSYYKLGASQRVAGDSGFAAYSRYR |
| IGNYKLNTDHSSSSDNIALLVQ |

What is claimed is:

1. An immunogenic composition comprising (a) at least two distinct polypeptides, each polypeptide consisting of at least 30 amino acids and no more than 60 amino acids and comprising an amino acid sequence selected from the group consisting of SEQ ID NOs: 1 to 17, and (b) a pharmaceutically-acceptable compound that increases immunogenicity of the polypeptides.

2. The immunogenic composition of claim 1, wherein the composition comprises:
   (a) at least one distinct polypeptide consisting of at least 30 amino acids and no more than 60 amino acid residues and comprising an amino sequence selected from SEQ ID NOs: 1 to 11;
   (b) at least one distinct polypeptide consisting of at least 30 amino acids and no more than 60 amino acids and comprising an amino sequence selected from SEQ ID NOs: 12 to 15;
   (c) at least one distinct polypeptide consisting of at least 30 amino acids and no more than 60 amino acids and comprising an amino sequence selected from SEQ ID NO: 16; and
   (d) at least one distinct polypeptide consisting of at least 30 amino acids and no more than 60 amino acids and comprising an amino sequence selected from SEQ ID NO: 17.

3. The immunogenic composition of claim 1, wherein the distinct amino acid sequence is selected from the group consisting of SEQ ID NOs: 2, 5, 7, 9, 12, 13, 14, 15, 16, and 17.

4. The immunogenic composition of claim 2, wherein the amino acid sequences are selected from the group consisting of SEQ ID NOs: 2, 5, 7, 9, 12, 13, 14, 15, 16, and 17.

5. The immunogenic composition of claim 1, wherein said composition comprises six distinct polypeptides, each polypeptide consisting of at least 30 amino acids and no more than 60 amino acids and comprising a distinct amino acid sequence selected from the group consisting of SEQ ID NOs: 2, 5, 7, 9, 12, 13, 14, 15, 16, and 17.

6. The immunogenic composition of claim 1, wherein said composition comprises eight distinct polypeptides, each polypeptide consisting of at least 30 amino acids and no more than 60 amino acids and comprising a distinct amino acid sequence selected from the group consisting of SEQ ID NOs: 2, 5, 7, 9, 12, 13, 14, 15, 16, and 17.

7. The immunogenic composition of claim 1, wherein said composition comprises ten distinct polypeptides, each polypeptide consisting of at least 30 amino acids and no more than 60 amino acids and comprising a distinct amino acid sequence selected from the group consisting of SEQ ID NOs: 2, 5, 7, 9, 12, 13, 14, 15, 16, and 17.

8. The immunogenic composition of claim 1, wherein the at least one polypeptide comprises a fragment of a Coronaviridae protein that is a CD8+ T cell epitope that is restricted to at least two HLA class I alleles of an individual.

9. The immunogenic composition of claim 1, wherein the at least one polypeptide comprises a fragment of a Coronaviridae protein that is a CD4+ T cell epitope restricted to at least two HLA class II alleles of an individual.

10. The immunogenic composition of claim 1, wherein the at least one polypeptide comprises a linear B cell epitope.

11. A method of stimulating an immune response against a SARS-CoV-2 infection in an individual in need thereof, comprising administering to the individual the immunogenic composition of claim 1.

12. The immunogenic composition of claim 1, wherein said composition comprises a polypeptide consisting of a sequence according to SEQ ID NO: 2, a polypeptide consisting of a sequence according to SEQ ID NO: 5, a polypeptide consisting of a sequence according to SEQ ID NO: 7, a polypeptide consisting of a sequence according to SEQ ID NO: 9, a polypeptide consisting of a sequence according to SEQ ID NO: 12, a polypeptide consisting of a sequence according to SEQ ID NO: 13, a polypeptide consisting of a sequence according to SEQ ID NO: 14, a polypeptide consisting of a sequence according to SEQ ID NO: 15, a polypeptide consisting of a sequence according to SEQ ID NO: 16, and a polypeptide consisting of a sequence according to SEQ ID NO: 17.

* * * * *